(12) United States Patent
Gammill

(10) Patent No.: US 6,821,977 B2
(45) Date of Patent: Nov. 23, 2004

(54) ANTIDIABETIC AGENTS

(75) Inventor: Ronald B. Gammill, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 9 days.

(21) Appl. No.: 10/368,916

(22) Filed: Feb. 19, 2003

(65) Prior Publication Data

US 2003/0199553 A1 Oct. 23, 2003

Related U.S. Application Data

(60) Provisional application No. 60/360,913, filed on Feb. 28, 2002.

(51) Int. Cl.[7] .................. C07D 495/06; C07D 407/12; C07D 407/14; A61K 31/407; A61K 31/353

(52) U.S. Cl. .................. 514/254.11; 548/453; 548/454; 544/377; 549/350; 546/197; 514/321; 514/414; 514/450; 540/552; 540/569

(58) Field of Search .................. 549/350; 548/453, 548/454; 544/377; 546/197; 514/254.11, 321, 414, 450

(56) References Cited

FOREIGN PATENT DOCUMENTS

| WO | WO 9639384 | 12/1996 |
|----|------------|---------|
| WO | WO 9639385 | 12/1996 |

OTHER PUBLICATIONS

Allard et al., Am. J. Physiol., 267:H66–H74, 1994.
Martin et al., Biochemistry, 30:10101, 1991.
Kasvinsky et al., J. Biol. Chem, 253: 3343–3351 and 9102–9106, 1978.
Blundell et al., Diabetologia, 35: Supp. 2, 569–576, 1992.

*Primary Examiner*—Richard L. Raymond
*Assistant Examiner*—Kahsay Habte
(74) *Attorney, Agent, or Firm*—Peter C. Richardson; Gregg C. Benson; Carl J. Goddard

(57) ABSTRACT

A compound of the formula

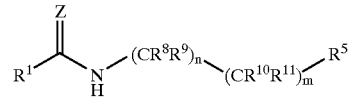

I whereon
$R_1$ is:

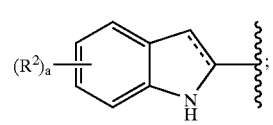

(i)

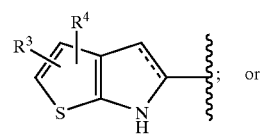

(ii)

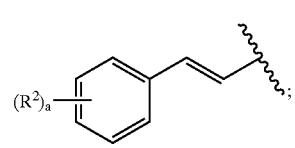

(iii)

$R^5$ is:

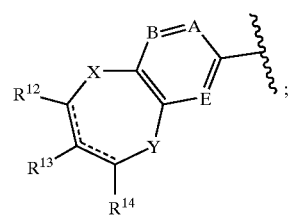

(iv)

and n, m, Z, $R^8$, $R^9$, $R^{10}$ and $R^{11}$ are as defined herein, useful in the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia.

10 Claims, No Drawings

ANTIDIABETIC AGENTS

CROSS REFERENCE TO RELATED APPLICATIONS

This application claims the benefit of United States Provisional Application No. 60/360,913, filed Feb. 28, 2002.

BACKGROUND OF THE INVENTION

The present invention relates to substituted 1H-(indole-2-carboxamides and 6H-thieno[2,3-b]pyrrole-5-Carboxamides which are antidiabetic agents and as such are useful in the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia.

This invention also relates to a method of using such compounds in the treatment of the above diseases in mammals, especially humans, and to the pharmaceutical compositions useful therefor.

In spite of the early discovery of insulin and its subsequent widespread use in the treatment of diabetes, and the later discovery of and use of sulfonylureas, biguanides and thiazolidinediones, such as troglitazone, rosiglitazone or pioglitazone, as oral hypoglycemic agents, the treatment of diabetes remains less than satisfactory.

The use of insulin requires multiple daily doses, usually by self injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidinediones, and in more severe cases, insulin. However, the clinically available hypoglycemic agents can have side effects that limit their use, or an agent may not be effective with a particular patient. In the case of insulin dependent diabetes mellitus (Type I), insulin is usually the primary course of therapy. Hypoglycemic agents that have fewer side effects or succeed where others fail are needed.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque," which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion that can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no marketed drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. The mechanism(s) responsible for the myocardial injury observed after ischemia and reperfusion is not fully understood. It has been reported (M. F. Allard, et al., Am. J. Physiol., 267: H66–H74 (1994)) that "pre ischemic glycogen reduction . . . is associated with improved post ischemic left ventricular functional recovery in hypertrophied rat hearts".

In addition to myocardial ischemia, other tissues can undergo ischemia and be damaged resulting in serious problems for the patient. Examples of such tissues include cardiac, brain, liver, kidney, lung, gut, skeletal muscle, spleen, pancreas, nerve, spinal cord, retina tissue, the vasculature, or intestinal tissue.

Hepatic glucose production is an important target for NIDDM therapy. The liver is the major regulator of plasma glucose levels in the post absorptive (fasted) state, and the rate of hepatic glucose production in NIDDM patients is significantly elevated relative to normal individuals. Likewise, in the postprandial (fed) state, where the liver has a proportionately smaller role in the total plasma glucose supply, hepatic glucose production is abnormally high in NIDDM patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in NIDDM. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule to release glucose-1-phosphate and a new shortened glycogen macromolecule. Several types of glycogen phosphorylase inhibitors have been reported to date: glucose and glucose analogs [Martin, J. L. et al., Biochemistry, 30:10101 (1991)]; caffeine and other purine analogs [Kasvinsky, P. J. et al., J. Biol. Chem., 253: 3343–3351 and 9102–9106 (1978)]; substituted N-(indole-2-carbonyl)-amides [PCT Publication Number WO 96/39385]; and substituted N-(indole-2-carbonyl)-glycinamides [PCT Publication Number WO 96/39384]. These compounds and glycogen phosphorylase inhibitors in general, have been postulated to be of use for the treatment of NIDDM by decreasing hepatic glucose production and lowering glycemia. [Blundell, T. B. et al., Diabetologia, 35: Suppl. 2, 569–576 (1992) and Martin et al., Biochemistry, 30: 10101 (1991)].

Myocardial ischemic injury can occur in outpatient as well as in perioperative settings and can lead to the development of sudden death, myocardial infarction or congestive heart failure. There is an unmet medical need to prevent or minimize myocardial ischemic injury, particularly perioperative myocardial infarction. Such a therapy is anticipated to be life-saving and reduce hospitalizations, enhance quality of life and reduce overall health care costs of high risk patients.

Although there are a variety of hyperglycemia, hypercholesterolemia, hypertension, hyperlipidemia, atherosclerosis and tissue ischemia therapies, there is a continuing need and a continuing search in this field of art for alternative therapies.

SUMMARY OF THE INVENTION

The present invention relates to a compound of the formula

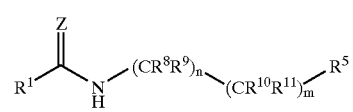

I or the pharmaceutically acceptable salt thereof; wherein
n is 0, 1, 2, 3 or 4;
m is 0, 1, 2, 3 or 4;
Z is oxygen or sulfur;
$R^1$ is

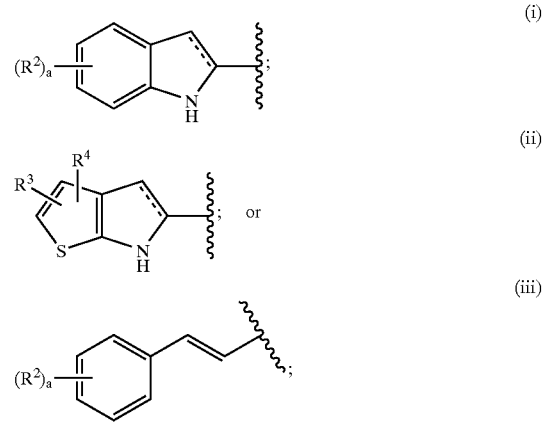

wherein the dashed lines represent optional double bonds;
a is 1, 2 or 3;
each $R^2$ is independently hydrogen, halo, hydroxy, amino, nitro, $(C_1–C_6)$alkoxy, cyano, C(O)H or $(C_1–C_6)$alkyl optionally substituted by one to three fluoro atoms;

$R^3$ is hydrogen, halo, cyano, $(C_1-C_6)$alkyl or $(C_1-C_3)$alkynyl;

$R^4$ is hydrogen, halo, cyano or $(C_1-C_6)$alkyl;

$R^5$ is

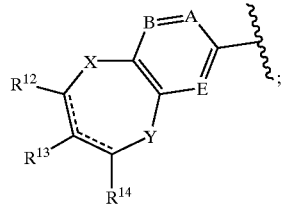

(iv)

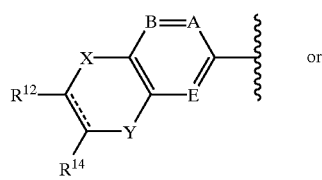

(v) or

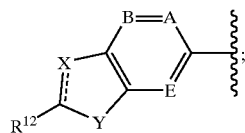

(vi)

wherein the dashed lines represent optional double bonds;

A, B and E are each independently nitrogen or CR15;

X and Y are each independently $CH_2$, oxygen, $S(O)_d$ wherein d is 0, 1 or 2; nitrogen or $NR^{16}$;

$R^8$, $R^9$, $R^{10}$ and $R^{11}$ are each independently hydrogen or $(C_1-C_6)$alkyl;

$R^{12}$ is hydrogen, $HC(O)(C_0-C_6)$alkyl, carboxy$(C_0-C_3)$alkyl, $R^{17}R^{18}N-C(O)-(C_0-C_3)$alkyl, hydroxy$(C_1-C_3)$alkyl, $R^{17}(C_1-C_3)$alkyl, $R^{17}R^{18}N(C_0-C_3)$alkyl, $(C_1-C_6)$alkyl-C(O)—NH, $(C_6-C_{10})$aryl-C(O)—NH, $(C_6-C_{10})$aryl$(C_1-C_6)$alkyl-C(O)—NH, $(C_2-C_9)$heteroaryl$(C_1-C_6)$alkyl-C(O)—NH, $(C_1-C_6)$alkylaminocarbonylamino, $(C_6-C_{10})$arylaminocarbonylamino, $(C_6-C_{10})$aryl$(C_1-C_6)$alkylaminocarbonylamino, $(C_2-C_9)$heteroaryl$(C_1-C_6)$alkylaminocarbonylamino, $(C_1-C_6)$alkylsulfonylamino, $(C_6-C_{10})$aryl$(C_1-C_6)$alkylsulfonylamino, $(C_2-C_9)$heteroarylsulfonylamino, $(C_2-C_9)$heteroaryl$(C_1-C_6)$alkylsulfonylamino, $(C_1-C_6)$alkylsulfonyl $N((C_1-C_6)$alkyl), $(C_6-C_{10})$aryl$(C_1-C_6)$alkylsulfonyl $N((C_1-C_6)$alkyl), $(C_2-C_9)$heteroarylsulfonyl $N((C_1-C_6)$alkyl), $(C_2-C_9)$heteroaryl$(C_1-C_6)$alkylsulfonyl $N((C_1-C_6)$alkyl), $(C_3-C_7)$cycloalkylamino, $((C_3-C_7)$cycloalkyl$)_2$amino, $(C_3-C_7)$cycloalkylcarbonylamino, $(C_6-C_{10})$aryl$(C_3-C_7)$cycloalkylcarbonylamino, $(C_2-C_9)$heteroaryl$(C_3-C_7)$cycloalkylcarbonylamino, $(C_3-C_7)$cycloalkylaminocarbonylamino, $(C_6-C_{10})$aryl$(C_3-C_7)$cycloalkylaminocarbonylamino, $(C_2-C_9)$heteroaryl$(C_3-C_7)$cycloalkylaminocarbonylamino, $(C_3-C_7)$cycloalkylsulfonylamino, $(C_6-C_{10})$aryl$(C_3-C_7)$cycloalkylsulfonylamino, $(C_2-C_9)$heteroaryl$(C_3-C_7)$cycloalkylsulfonylamino, $(C_3-C_7)$cycloalkylsulfonyl $N((C_3-C_7)$cycloalkyl), $(C_6-C_{10})$aryl$(C_3-C_7)$cycloalkylsulfonyl $N((C_3-C_7)$cycloalkyl, $(C_2-C_9)$heteroarylsulfonyl $N((C_3-C_7)$cycloalkyl), $(C_2-C_9)$heteroaryl$(C_3-C_7)$cycloalkylsulfonyl $N((C_3-C_7)$cycloalkyl), $(C_1-C_6)$alkyl $S(O)_c$, $(C_3-C_7)$cycloalkyl $S(O)_c$, $(C_6-C_{10})$aryl$(C_1-C_6)$alkyl $S(O)_c$, $(C_6-C_{10})$aryl $S(O)_c$, $(C_1-C_6)$alkylamino $S(O)_c$, $(C_1-C_6)$arylamino $S(O)_c$, $(C_6-C_{10})$aryl$C_1-C_6)$alkylamino $S(O)_c$ wherein c is 0, 1 or 2;

$R^{13}$ is hydrogen or $(C_1-C_6)$alkyl;

$R^{14}$ is hydrogen, hydroxy, $(C_1-C_6)$alkoxy, $(C_6-C_{10})$aryloxy or $NR^{17}R^{18}$;

$R^{15}$ is hydrogen, $(C_1-C_6)$alkylcarbonylcarboxy, hydroxy $(C_1-C_6)$alkyl, $(C_1-C_6)$alkyl piperazinylcarbonyl or piperidinylcarbonyl;

$R^{16}$ is hydrogen, HCO, $(C_1-C_6)$alkyl, $(C_1-C_6)$alkoxycarbonyl$(C_1-C_6)$alkyl, carboxy$(C_1-C_6)$alkyl, piperidinyl$(C_1-C_6)$alkylcarbonyl; $(C_1-C_6)$acyl; piperidinyl carbonyl$(C_1-C_6)$alkyl, hydroxy$(C_1-C_6)$alkyl, halo$(C_1-C_6)$alkylcarbonyl or morpholinyl$(C_1-C_6)$alkylcarbony;

$R^{17}$ and $R^{18}$ are each independently hydrogen, $(C_1-C_6)$alkyl, $(C_6-C_{10})$aryl$(C_1-C_6)$alkyl and $(C_2-C_9)$heteroaryl $(C_1-C_6)$alkyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "heteroaryl", as used herein, unless otherwise indicated, includes an organic radical derived from an aromatic heterocycle by removal of one hydrogen, such as furyl, thienyl, pyrrolyl, oxazolyl, isoxazolyl, thiazolyl, isothiazolyl, pyrazolyl, imidazolyl, oxadiazolyl, thiadiazolyl, triazolyl, pyridinyl, pyridazinyl, pyrimidinyl, pyrazinyl, benzofuryl, benzothienyl, indolyl, isoindolyl, benzoxazolyl, benzothiazolyl, benzimidazolyl, quinolinyl, isoquinolinyl, cinnolinyl, quinazolinyl, quinoxalinyl, thienopyrrolyl or azaindolyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

Preferred compounds of formula I include those wherein $R^1$ is

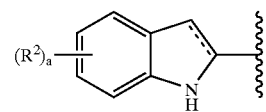

(i)

wherein a is 1 or 2; and each $R^2$ is independently halo, amino or $(C_1-C_6)$alkyl optionally substituted by one to three fluoro atoms.

Preferred compounds of formula I include those wherein n is 0, 1, 2 or 3; m is 0, 1, 2 or 3; and Z is oxygen.

Preferred compounds of formula I include those wherein $R^5$ is

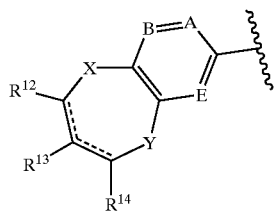

(iv)

wherein A, B and E are $CR^{15}$;
X is oxygen or nitrogen;
Y is oxygen or $NR^{16}$;
$R^{12}$ is hydrogen, $(C_1-C_6)$alkyl, hydroxy$(C_1-C_6)$alkyl or carboxy;
$R^{15}$ is hydrogen, $(C_1-C_6)$alkylcarbonylcarboxy, hydroxy $(C_1-C_6)$alkyl, $(C_1-C_6)$alkyl piperazinylcarbonyl or piperidinylcarbonyl;
$R^{16}$ is HCO, $(C_1-C_6)$alkyl, $(C_1-C_6)$alkoxycarbonyl $(C_1-C_6)$alkyl, carboxy$(C_1-C_6)$alkyl, piperidinyl$(C_1-C_6)$alkylcarbonyl; $(C_1-C_6)$acyl; piperidinyl carbonyl$(C_1-C_6)$alkyl, hydroxy$(C_1-C_6)$alkyl, halo$(C_1-C_6)$alkylcarbonyl or morpholinyl$(C_1-C_6)$alkylcarbonyl.

Other preferred compounds of formula I include those wherein $R^5$ is

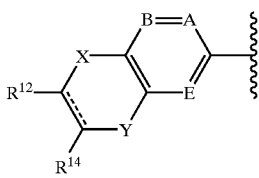

(v)

wherein A is $CR^{15}$;
B and E are each independently $CR^{15}$ or nitrogen; and
X and Y are each independently nitrogen or $CH_2$.

Other preferred compounds of formula I include those wherein $R^5$ is

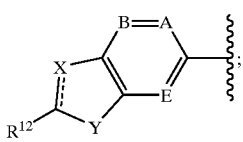

(vi)

wherein A is $CR^{15}$;
B and E are each independently oxygen or nitrogen; and
X and Y are each independently nitrogen or $CH_2$.

Most preferred compounds of formula I include those wherein $R^1$ is

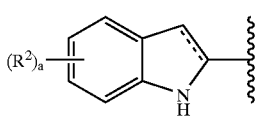

(i)

wherein a is 1 or 2; and each $R^2$ is independently halo, amino or $(C_1-C_6)$alkyl optionally substituted by one to three fluoro atoms; n is 0, 1, 2 or 3; m is 0, 1, 2 or 3; Z is oxygen and $R^5$ is

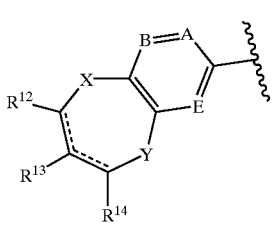

(iv)

wherein A, B and E are $CR^{15}$;
X is oxygen or nitrogen;
Y is oxygen or $NR^{16}$;

$R^{12}$ is hydrogen, $(C_1-C_6)$alkyl, hydroxy$(C_1-C_6)$alkyl or carboxy;
$R^{15}$ is hydrogen, $(C_1-C_6)$alkylcarbonylcarboxy, hydroxy $(C_1-C_6)$alkyl, $(C_1-C_6)$alkyl piperazinylcarbonyl or piperidinylcarbonyl;
$R^{16}$ is HCO, $(C_1-C_6)$alkyl, $(C_1-C_6)$alkoxycarbonyl $(C_1-C_6)$alkyl, carboxy$(C_1-C_6)$alkyl, piperidinyl$(C_1-C_6)$alkylcarbonyl; $(C_1-C_6)$acyl; piperidinyl carbonyl$(C_1-C_6)$alkyl, hydroxy$(C_1-C_6)$alkyl, halo$(C_1-C_6)$alkylcarbonyl or morpholinyl$(C_1-C_6)$alkylcarbonyl.

Most preferred compounds of formula I include those wherein $R^1$ is

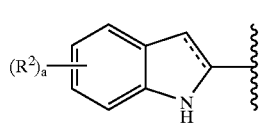

(i)

wherein a is 1 or 2; and each $R^2$ is independently halo, amino or $(C_1-C_6)$alkyl optionally substituted by one to three fluoro atoms; n is 0, 1, 2 or 3; m is 0, 1, 2 or 3; Z is oxygen and $R^5$ is

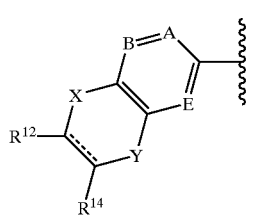

(v)

wherein A is $CR^{15}$;
B and E are each independently $CR^{15}$ or nitrogen; and
X and Y are each independently nitrogen or $CH_2$.

Most preferred compounds of formula I include those wherein $R^1$ is

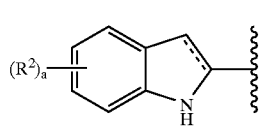

(i)

wherein a is 1 or 2; and each $R^2$ is independently halo, amino or $(C_1-C_6)$alkyl optionally substituted by one to three fluoro atoms; n is 0, 1, 2 or 3; m is 0, 1, 2 or 3; Z is oxygen and $R^5$ is

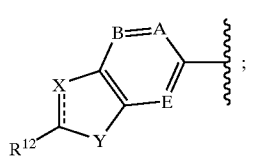

(vi)

wherein A is $CR^{15}$;
B and E are each independently $CR^{15}$ or nitrogen; and
X and Y are each independently nitrogen or $CH_2$.

Specific preferred compounds of formula I include those wherein said compound is selected from the group consisting of:

5-Chloro-1H-indole-2-carboxylic acid (4-hydroxymethyl-6,7,8,9-tetrahydro-5-oxa-9-aza-benzocyclohepten-2-yl)-amide;

5-Chloro-1H-indole-2-carboxylic acid (9-methanesulfonylamino-3,4-dihydro-2H-benzo[b][1,4]dioxepin-7-yl)-amide;

5-Chloro-1H-indole-2-carboxylic acid (9-hydroxymethyl-3,4-dihydro-2H-benzo[b][1,4]dioxepin-7-yl)-amide;

{8-[(5-Chloro-1H-indole-2-carbonyl)-amino]-3,4-dihydro-2H-benzo[b][1,4]dioxepin-6-ylamino}-acetic acid ethyl ester;

{2-[(5-Chloro-1H-indole-2-carbonyl)-amino]-4-hydroxymethyl-7,8-dihydro-6H-5-oxa-9-aza-benzocyclohepten-9-yl}-acetic acid;

5-Chloro-1H-indole-2-carboxylic acid (9-amino-3,4-dihydro-2H-benzo[b][1,4]dioxepin-7-yl)-amide;

5-Chloro-1H-indole-2-carboxylic acid [9-(2-hydroxy-ethyl)-6,7,8,9-tetrahydro-5-oxa-9-aza-benzocyclohepten-2-yl]-amide;

{2-[(5-Chloro-1H-indole-2-carbonyl)-amino]-7,8-dihydro-6H-5-oxa-9-aza-benzocyclohepten-9-yl}-acetic acid;

5-Methyl-1H-indole-2-carboxylic acid (9-hydroxymethyl-3,4-dihydro-2H-benzo[b][1,4]dioxepin-7-yl)-amide;

5-Chloro-1H-indole-2-carboxylic acid {9-[2-(3,4-dihydroxy-pyrrolidin-1-yl)-2-oxo-ethyl]-6,7,8,9-tetrahydro-5-oxa-9-aza-benzocyclohepten-2-yl}-amide;

5-Chloro-1H-indole-2-carboxylic acid [4-(piperidine-1-carbonyl)-6,7,8,9-tetrahydro-5-oxa-9-aza-benzocyclohepten-2-yl]-amide;

5-Chloro-1H-indole-2-carboxylic acid (3,4-dihydro-2H-benzo[1,4]oxazin-6-yl)-amide;

5-Chloro-1H-indole-2-carboxylic acid (3,5-dichloro-4-hydroxy-phenyl)-amide;

5-Fluoro-1H-indole-2-carboxylic acid (6,7,8,9-tetrahydro-5-oxa-9-aza-benzocyclohepten-2-yl)-amide;

5-Chloro-1H-indole-2-carboxylic acid [9-(2-hydroxyethylcarbamoyl)-3,4-dihydro-2H-benzo[b][1,4]dioxepin-7-yl]-amide;

5-Chloro-1H-indole-2-carboxylic acid (6,7,8,9-tetrahydro-5-oxa-9-aza-benzocyclohepten-2-yl)-amide;

5-Chloro-1H-indole-2-carboxylic acid (9-methyl-6,7,8,9-tetrahydro-5-oxa-9-aza-benzocyclohepten-2-yl)-amide;

2-[(5-Chloro-1H-indole-2-carbonyl)-amino]-6,7,8,9-tetrahydro-5-oxa-9-aza-benzocycloheptene-4-carboxylic acid;

5-Chloro-1H-indole-2-carboxylic acid (3-hydroxy-4-methoxy-phenyl)-amide;

5-Chloro-1H-indole-2-carboxylic acid (3,4-dihydro-2H-benzo[b][1,4]dioxepin-7-yl)-amide;

5-Methyl-1H-indole-2-carboxylic acid (6,7,8,9-tetrahydro-5-oxa-9-aza-benzocyclohepten-2-yl)-amide;

5-Chloro-1H-indole-2-carboxylic acid (9-dimethylcarbamoyl-3,4-dihydro-2H-benzo[b][1,4]dioxepin-7-yl)-amide;

5-Chloro-1H-indole-2-carboxylic acid [9-(2-oxo-2-pyrrolidin-1-yl-ethyl)-6,7,8,9-tetrahydro-5-oxa-9-aza-benzocyclohepten-2-yl]-amide;

5-Bromo-1H-indole-2-carboxylic acid (3,4-dihydro-2H-benzo[b][1,4]dioxepin-7-yl)-amide;

5-Methyl-1H-indole-2-carboxylic acid (2,3,4,5-tetrahydro-benzo[b]dioxocin-8-yl)-amide;

8-[(5-Chloro-1H-indole-2-carbonyl)-amino]-3,4-dihydro-2H-benzo[b][1,4]dioxepine-6-carboxylic acid;

5-Methyl-1H-indole-2-carboxylic acid (3,4-dihydro-2H-benzo[b][1,4]dioxepin-7-yl)-amide;

5-Chloro-1H-indole-2-carboxylic acid [9-(3,4-dihydroxy-pyrrolidine-1-carbonyl)-3,4-dihydro-2H-benzo[b][1,4]dioxepin-7-yl]-amide;

5-Chloro-1H-indole-2-carboxylic acid [4-(4-methyl-piperazine-1-carbonyl)-6,7,8,9-tetrahydro-5-oxa-9-aza-benzocyclohepten-2-yl]-amide;

1H-Indole-2-carboxylic acid (9-hydroxymethyl-3,4-dihydro-2H-benzo[b][1,4]dioxepin-7-yl)-amide;

1H-Indole-2-carboxylic acid (3,4-dihydro-2H-benzo[b][1,4]dioxepin-7-yl)-amide;

5-Chloro-1H-indole-2-carboxylic acid [9-(4-methyl-piperazine-1-carbonyl)-3,4-dihydro-2H-benzo[b][1,4]dioxepin-7-yl]-amide;

5-Fluoro-1H-indole-2-carboxylic acid (3,4-dihydro-2H-benzo[b][1,4]dioxepin-7-yl)-amide;

5-Chloro-1H-indole-2-carboxylic acid {9-[(2-hydroxy-ethylcarbamoyl)-methyl]-6,7,8,9-tetrahydro-5-oxa-9-aza-benzocyclohepten-2-yl}-amide;

2-[(5-Chloro-1H-indole-2-carbonyl)-amino]-6,7,8,9-tetrahydro-5-oxa-9-aza-benzocycloheptene-4-carboxylic acid methyl ester;

5-Chloro-1H-indole-2-carboxylic acid [9-(2-hydroxy-ethyl)-4-hydroxymethyl-6,7,8,9-tetrahydro-5-oxa-9-aza-benzocyclohepten-2-yl]-amide;

1H-Indole-2-carboxylic acid (2,3,4,5-tetrahydro-benzo[b]dioxocin-8-yl)-amide; and 5-Fluoro-1H-indole-2-carboxylic acid (2,3,4,5-tetrahydro-benzo[b]dioxocin-8-yl)-amide.

Also provided are pharmaceutical compositions comprising a compound of Formula I, stereoisomers, pharmaceutically acceptable salts and prodrugs thereof, and pharmaceutically acceptable salts of the prodrugs.

Also provided are methods of treating or preventing atherosclerosis, the methods comprising the step of administering to a patient having atherosclerosis or at risk of having atherosclerosis a therapeutically effective amount of a compound of Formula I, stereoisomers, pharmaceutically acceptable salts and prodrugs thereof, and pharmaceutically acceptable salts of the prodrugs.

Also provided are methods of treating diabetes, the methods comprising the step of administering to a patient having diabetes a therapeutically effective amount of a compound of Formula I, stereoisomers, pharmaceutically acceptable salts and prodrugs thereof, and pharmaceutically acceptable salts of the prodrug.

In a preferred embodiment of the methods of treating diabetes, the diabetes is non-insulin dependent diabetes mellitus (Type II).

In another preferred embodiment of the methods of treating diabetes, the diabetes is insulin dependent diabetes mellitus (Type I).

Also provided are methods of treating insulin resistance, the methods comprising the step of administering to a patient having insulin resistance a therapeutically effective amount of a compound of Formula I, stereoisomers, pharmaceutically acceptable salts and prodrugs thereof, and pharmaceutically acceptable salts of the prodrugs.

Also provided are methods of treating diabetic neuropathy, the methods comprising the step of administering to a patient having diabetic neuropathy a therapeutically effective amount of a compound of Formula I, stereoisomers, pharmaceutically acceptable salts and prodrugs thereof, and pharmaceutically acceptable salts of the prodrugs.

Also provided are methods of treating diabetic nephropathy, the methods comprising the step of administering to a patient having diabetic nephropathy a therapeutically effective amount of a compound of Formula I, stereoisomers, pharmaceutically acceptable salts and prodrugs thereof, and pharmaceutically acceptable salts of the prodrugs.

Also provided are methods of treating diabetic retinopathy, the methods comprising the step of administering to a patient having diabetic retinopathy a therapeutically effective amount of a compound of Formula I, stereoisomers, pharmaceutically acceptable salts and prodrugs thereof, and pharmaceutically acceptable salts of the prodrugs.

Also provided are methods of treating cataracts, the methods comprising the step of administering to a patient having cataracts a therapeutically effective amount of a compound of Formula I, stereoisomers, pharmaceutically acceptable salts and prodrugs thereof, and pharmaceutically acceptable salts of the prodrugs.

Also provided are methods of treating or preventing hypercholesterolemia, the methods comprising the step of administering to a patient having hypercholesterolemia or at risk of having hypercholesterolemia a therapeutically effective amount of a compound of Formula I, stereoisomers, pharmaceutically acceptable salts and prodrugs thereof, and pharmaceutically acceptable salts of the prodrugs.

Also provided are methods of treating or preventing hypertriglyceridemia, the methods comprising the step of administering to a patient having hypertriglyceridemia or at risk of having hypertriglyceridemia a therapeutically effective amount of a compound of Formula I, stereoisomers, pharmaceutically acceptable salts and prodrugs thereof, and pharmaceutically acceptable salts of the prodrugs.

Also provided are methods of treating or preventing hyperlipidemia, the methods comprising the step of administering to a patient having hyperlipidemia or at risk of having hyperlipidemia a therapeutically effective amount of a compound of Formula I, stereoisomers, pharmaceutically acceptable salts and prodrugs thereof, and pharmaceutically acceptable salts of the prodrugs.

Also provided are methods of treating hyperglycemia, the methods comprising the step of administering to a patient having hyperglycemia or at risk of having hyperglycemia therapeutically effective amount of a compound of Formula I, stereoisomers, pharmaceutically acceptable salts and prodrugs thereof, and pharmaceutically acceptable salts of the prodrugs.

Also provided are methods of treating hypertension, the methods comprising the step of administering to a patient having hypertension or at risk of having hypertension a therapeutically effective amount of a compound of Formula I, stereoisomers, pharmaceutically acceptable salts and prodrugs thereof, and pharmaceutically acceptable salts of the prodrugs.

Also provided are methods of treating or preventing tissue ischemia, the methods comprising the step of administering to a patient having tissue ischemia or at risk of having tissue ischemia a therapeutically effective amount of a compound of Formula I, stereoisomers, pharmaceutically acceptable salts and prodrugs thereof, and pharmaceutically acceptable salts of the prodrugs.

Also provided are methods of treating or preventing myocardial ischemia, the methods comprising the step of administering to a patient having myocardial ischemia or at risk of having myocardial ischemia a therapeutically effective amount of a compound of Formula I, stereoisomers, pharmaceutically acceptable salts and prodrugs thereof, and pharmaceutically acceptable salts of the prodrugs.

Also provided are methods of inhibiting glycogen phosphorylase, the methods comprising the step of administering to a patient in need of glycogen phosphorylase inhibition, a glycogen phosphorylase inhibiting amount of a compound of Formula I, stereoisomers, pharmaceutically acceptable salts and prodrugs thereof, and pharmaceutically acceptable salts of the prodrugs.

Also provided are kits for the treatment of diabetes, insulin resistance, diabetic neuropathy, diabetic nephropathy, diabetic retinopathy, or cataracts in a patient having diabetes, insulin resistance, diabetic neuropathy, diabetic nephropathy, diabetic retinopathy, or cataracts, the kits comprising:

a) a first pharmaceutical composition comprising a compound of Formula I, stereoisomers, pharmaceutically acceptable salts and prodrugs of the compounds of Formula I, and pharmaceutically acceptable salts of the prodrugs;

b) a second pharmaceutical composition comprising a second compound useful for the treatment of diabetes, insulin resistance, diabetic neuropathy, diabetic nephropathy, diabetic retinopathy, or cataracts; and c) a container for containing the first and second compositions.

In a preferred embodiment of the kits, the second compound is selected from:

insulin and insulin analogs;
GLP-1 (7-37) (insulinotropin) and GLP-1 (7-36)-$NH_2$;
sulfonylureas and analogs;
biguanides;
$\alpha 2$-antagonists;
imidazolines;
glitazones (thiazolidinediones);
PPAR-gamma agonists;
fatty acid oxidation inhibitors;
$\alpha$-glucosidase inhibitors;
$\beta$-agonists;
phosphodiesterase Inhibitors;
lipid-lowering agents:
antiobesity agents
vanadate, vanadium complexes and peroxovanadium complexes;
amylin antagonists;
glucagon antagonists;
gluconeogenesis inhibitors;
somatostatin analogs and antagonists; and
antilipolytic agents.

In another preferred embodiment of the kits, the second compound is selected from LysPro insulin, GLP-1 (7-37) (insulinotropin), GLP-1 (7-36)-$NH_2$, chlorpropamide, glibenclamide, tolbutamide, tolazamide, acetohexamide, glypizide, glimepiride, repaglinide, meglitinide; mefformin, phenformin, buformin, midaglizole, isaglidole, deriglidole, idazoxan, efaroxan, fluparoxan, linogliride, ciglitazone, pioglitazone, englitazone, troglitazone, darglitazone, rosiglitazone, clomoxir, etomoxir, acarbose, miglitol, emiglitate, voglibose, MDL-25,637, camiglibose, MDL-73, 945, BRL 35135, BRL 37344, Ro 16-8714, ICI D7114, CL 316,243, L-386,398; benfluorex, fenfluramine, Naglivan®, acipimox, WAG 994, Symlin™, AC2993 and nateglinide.

In still another preferred embodiment of the kits, the second compound is selected from insulin, sulfonylureas, biguanides, and thiazolidinediones.

Also provided are kits for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia in a patient having diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, the kits comprising:

a) a first pharmaceutical composition comprising a compound of Formula I, stereoisomers, pharmaceutically acceptable salts and prodrugs of the compounds of Formula I, and pharmaceutically acceptable salts of the prodrugs;
b) a second pharmaceutical composition comprising a second compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia; and
c) a container for containing the first and second compositions.

Also provided are methods of treating diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, the method comprising the step of administering to a patient having diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, a therapeutically effective amount of a compound of Formula I, stereoisomers, pharmaceutically acceptable salts and prodrugs thereof, and pharmaceutically acceptable salts of the prodrugs in combination with at least one additional compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

Also provided are pharmaceutical compositions comprising a compound of Formula I, stereoisomers, pharmaceutically acceptable salts and prodrugs thereof, and pharmaceutically acceptable salts of the prodrugs and at least one additional compound useful to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

DETAILED DESCRIPTION OF THE INVENTION

The following reaction Schemes illustrate the preparation of the compounds of the present invention. Unless otherwise indicated a, n, m, A, B, E, $R^2$, $R^5$, $R^8$, $R^9$, $R^{10}$, $R^{11}$, $R^{12}$, $R^{13}$ and $R^{14}$ in the reaction Schemes and the discussion that follow are defined as above.

Preparation A

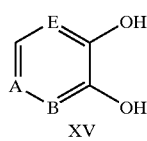
XV

↓ 1

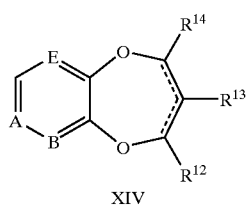
XIV

↓ 2

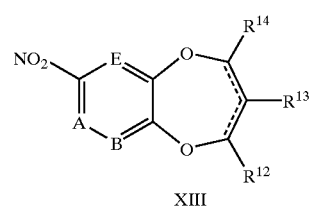
XIII

↓ 3

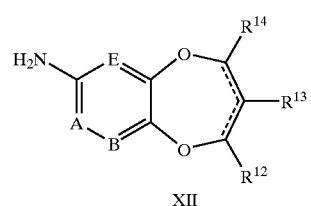
XII

Preparation B

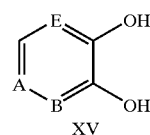
XV

↓ 1

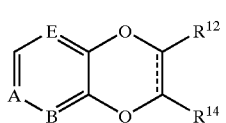
XVIII

↓ 2

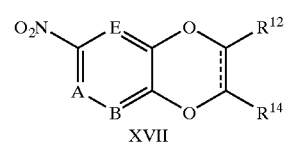
XVII

↓ 3

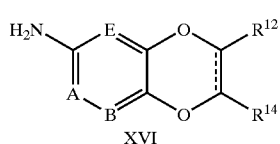
XVI

US 6,821,977 B2
15
-continued
Preparation C
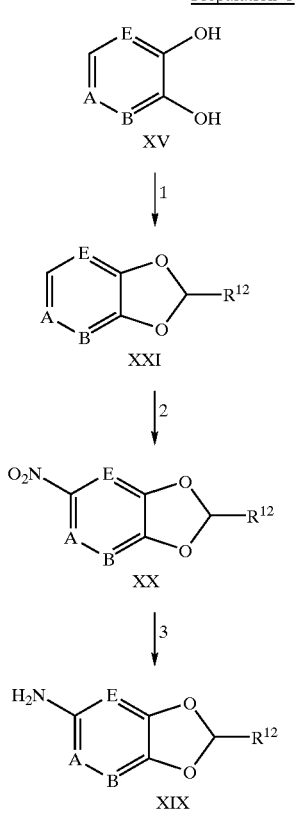
16
-continued
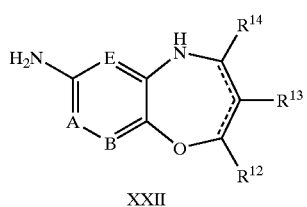
Preparation E
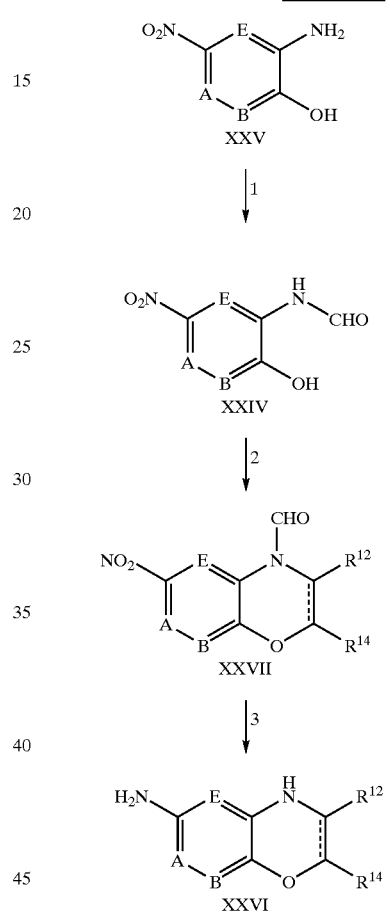
Preparation D
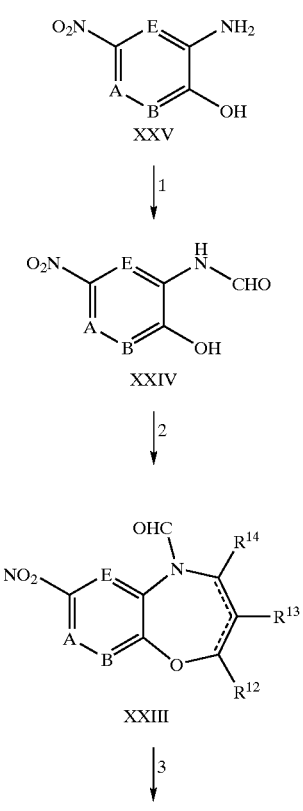
Preparation F
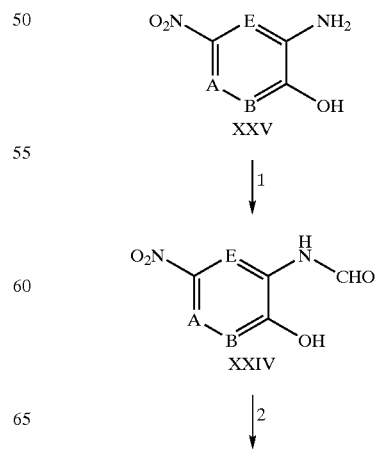

-continued
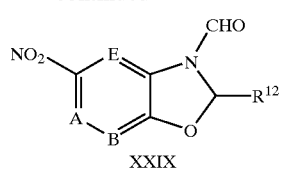
XXIX
↓3
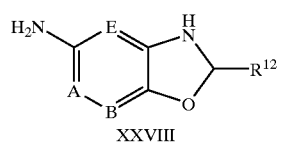
XXVIII
Preparation G
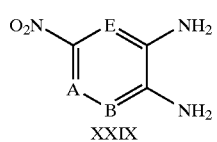
XXIX
↓1
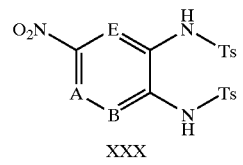
XXX
↓2
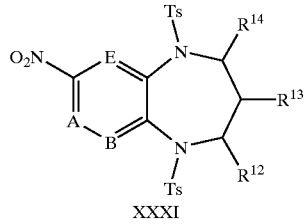
XXXI
↓
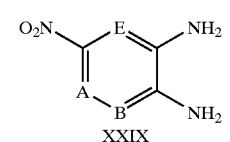
XXXII
Preparation H
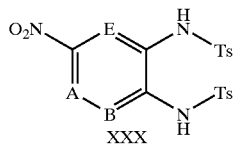
XXIX
↓1
-continued
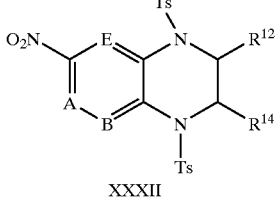
XXX
↓2
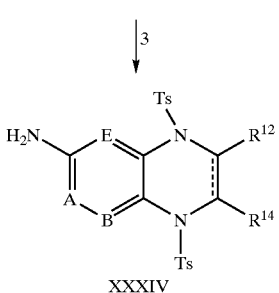
XXXII
↓3
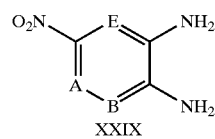
XXXIV
Preparation I
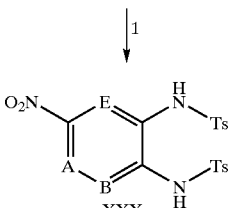
XXIX
↓1
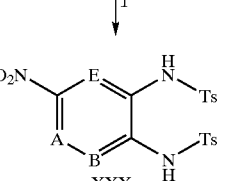
XXX
↓2
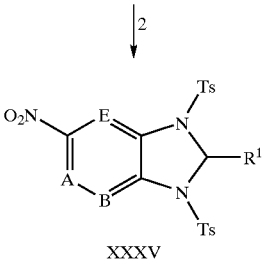
XXXV
↓3
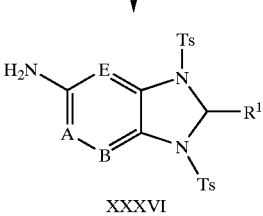
XXXVI -continued
Preparation J
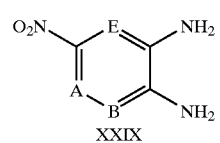
XXIX
↓1
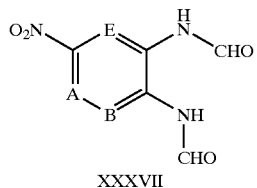
XXXVII
↓2
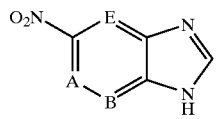
XXXVIII
Preparation K
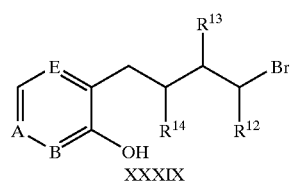
XXXIX
↓1
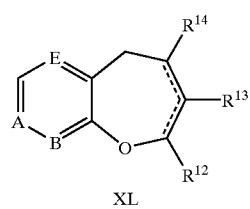
XL
Preparation L
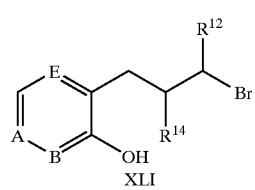
XLI
↓1
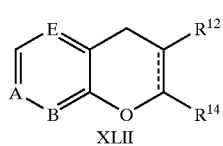
XLII
-continued
Preparation M
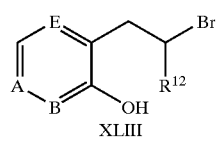
XLIII
↓1
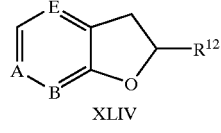
XLIV
Preparation N
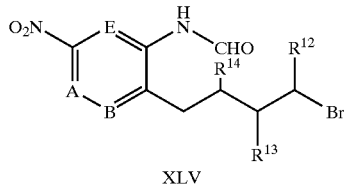
XLV
↓1
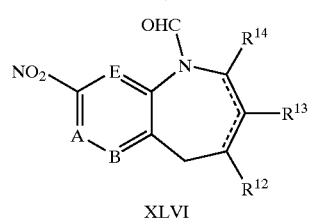
XLVI
Preparation O
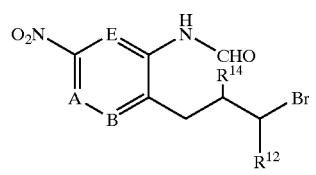
XLVII
↓1
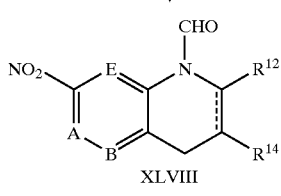
XLVIII
Preparation P
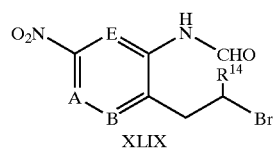
XLIX
↓1

-continued

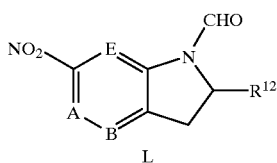

Scheme 1

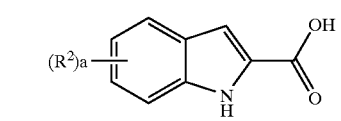
IV

↓1

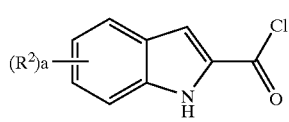
III

↓2

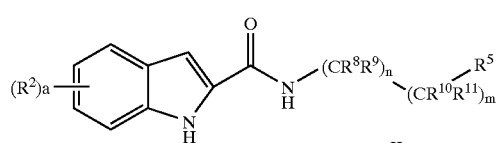
II

Scheme 2

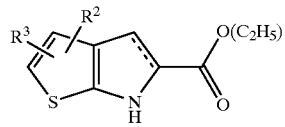
VIII

↓1

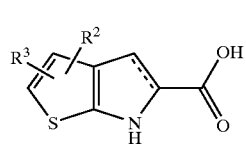
VII

↓2

-continued

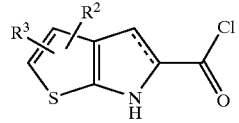
VI

↓3

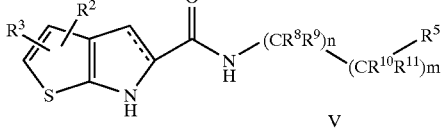
V

Scheme 3

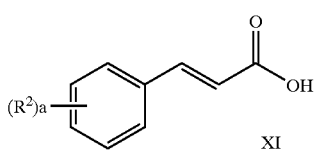
XI

↓1

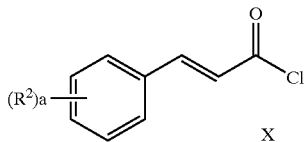
X

↓2

IX

In reaction 1 of Preparation A, the diol compound of formula XV is converted to the corresponding compound of formula XIV by reacting XV with a compound of the formula, Br—$CHR^{12}$—$CHR^{13}$—$CHR^{14}$—Cl, in the presence of potassium carbonate and a polar protic solvent, such as dimethylformamide. The reaction is stirred at a temperature between about 25° C. to about 100° C., preferably about 100° C., for a time period between about 1 hours to about 14 hours, preferably about 12 hours.

In reaction 2 of Preparation A, the compound of formula XIV is converted to the corresponding nitro compound of formula XIII by reacting XIV with nitric acid in the presence of an acetic acid/acetic anhydride mixture. The reaction is stirred at a temperature between about 0° C. to about 25° C., preferably about 10° C., for a time period between about 1 hours to about 6 hours, preferably about 2 hours.

In reaction 3 of Preparation A, the nitro compound of formula XIII is converted to the corresponding amino compound of formula XII by reducing XIII with ammonium formate in the presence of a catalyst, such as palladium on carbon, and an ether/alcohol mixture. The reaction is stirred at a temperature between about 0° C. to about 75° C., preferably about 50° C., for a time period between about 1 hours to about 6 hours, preferably about 4 hours.

In reaction 1 of Preparation B, the diol compound of formula XV is converted to the corresponding compound of formula XVIII by reacting XV with a compound of the formula, Br—$CHR^{12}$—$CHR^{14}$—Cl, according to the procedure described above in reaction 1 of Preparation A.

In reaction 2 of Preparation B, the compound of formula XVIII is converted to the corresponding nitro compound of formula XVII according to the procedure described above in reaction 2 of Preparation A.

In reaction 3 of Preparation B, the nitro compound of formula XVII is converted to the corresponding amino compound of formula XVI according to the procedure described above in reaction 3 of Preparation A.

In reaction 1 of Preparation C, the diol compound of formula XV is converted to the corresponding compound of formula XXI by reacting XV with a compound of the formula, Br—$CHR^{12}$—Cl, according to the procedure described above in reaction 1 of Preparation A.

In reaction 2 of Preparation C, the compound of formula XXI is converted to the corresponding nitro compound of formula XX according to the procedure described above in reaction 2 of Preparation A.

In reaction 3 of Preparation C, the nitro compound of formula XX is converted to the corresponding amino compound of formula XIX according to the procedure described above in reaction 3 of Preparation A.

In reaction 1 of Preparation D, the compound of formula XXV is converted to the corresponding compound of formula XXIV by reacting XXV with HCOONa. The reaction is stirred at a temperature between about 0° C. to about 75° C., preferably about 50° C., for a time period between about 1 hours to about 6 hours, preferably about 5 hours.

In reaction 2 of Preparation D, the compound of formula XXIV is converted to the corresponding compound of formula XXIII according to the procedure described above in reaction 1 of Preparation A.

In reaction 3 of Preparation D, the compound of formula XXIII is converted to the corresponding compound of formula XXII according to the procedure described above in reaction 3 of Preparation A.

In reaction 1 of Preparation E, the compound of formula XXV is converted to the corresponding compound of formula XXIV according to the procedure described above in reaction 1 of Preparation D.

In reaction 2 of Preparation E, the compound of formula XXIV is converted to the corresponding compound of formula XXVII according to the procedure described above in reaction 1 of Preparation B.

In reaction 3 of Preparation E, the nitro compound of formula XXVII is converted to the corresponding amino compound of formula XXVI according to the procedure described above in reaction 3 of Preparation A.

In reaction 1 of Preparation F, the compound of formula XXV is converted to the corresponding compound of formula XXIV according to the procedure described above in reaction 1 of Preparation D.

In reaction 2 of Preparation F, the compound of formula XXIV is converted to the corresponding compound of formula XXIX according to the procedure described above in reaction 1 of Preparation C.

In reaction 3 of Preparation F, the compound of formula XXIX is converted to the corresponding compound of formula XXVIII according to the procedure described above in reaction 3 of Preparation A.

In reaction 1 of Preparation G, the diamine compound of formula XXIX is converted to the corresponding compound of formula XXX by reacting XXIX with a compound of the formula, p-MePhSO$_2$Cl, in an anhydrous amine solvent such as pyridine. The reaction was stirred at a temperature between 25° C. to about 110° C., preferably about 100° C., for a time period between about 2 hours to about 6 hours, preferably about 4 hours.

In reaction 2 of Preparation G, the compound of formula XXX is converted to the corresponding compound of formula XXXI by reacting XXX with 1,3-dibromopropane in the presence of n-butanol and sodium metal. The reaction was stirred at a temperature between 0° C. to about 150° C., preferably about 125° C., for a time period between about 8 hours to about 30 hours, preferably about 24 hours.

In reaction 3 of Preparation G, the nitro compound of formula XVII is converted to the corresponding amino compound of formula XVI according to the procedure described above in reaction 3 of Preparation A.

In reaction 1 of Preparation H, the diamine compound of formula XXIX is converted to the corresponding compound of formula XXX by reacting XXIX with a compound of the formula, pMePhSO$_2$Cl, in an anhydrous amine solvent such as pyridine. The reaction was stirred at a temperature between 25° C. to about 110° C., preferably about 100° C., for a time period between about 2 hours to about 6 hours, preferably about 4 hours.

In reaction 2 of Preparation H, the compound of formula XXX is converted to the corresponding compound of formula XXXII by reacting XXX with 1,2-dibromoethane in the presence of n-butanol and sodium metal. The reaction was stirred at a temperature between 0° C. to about 150° C., preferably about 125° C., for a time period between about 8 hours to about 30 hours, preferably about 24 hours.

In reaction 3 of Preparation H, the nitro compound of formula XXXII is converted to the corresponding amino compound of formula XXXIV according to the procedure described above in reaction 3 of Preparation A.

In reaction 1 of Preparation I, the diamine compound of formula XXIX is converted to the corresponding compound of formula XXX by reacting XXIX with a compound of the formula, NO$_2$PhSO$_2$Cl, in an anhydrous amine solvent such as pyridine. The reaction was stirred at a temperature between 25° C. to about 110° C., preferably about 100° C., for a time period between about 2 hours to about 6 hours, preferably about 4 hours.

In reaction 2 of Preparation I, the compound of formula XXX is converted to the corresponding compound of formula XXXV by reacting XXX with ethyl 1,1-dichloroacetate in the presence of n-butanol and sodium metal. The reaction was stirred at a temperature between 0° C. to about 150° C., preferably about 125° C., for a time period between about 8 hours to about 30 hours, preferably about 24 hours.

In reaction 3 of Preparation I, the nitro compound of formula XXXV is converted to the corresponding amino compound of formula XXXVI according to the procedure described above in reaction 3 of Preparation A.

In reaction 1 of Preparation J, the diamine compound of formula XXIX is converted to the corresponding compound of formula XXXVII by reacting XXIX with sodium formate in concentrated formic acid. The reaction was stirred at a temperature between 25° C. to about 110° C., preferably about 100° C., for a time period between about 1 hours to about 4 hours, preferably about 2 hours.

In reaction 2 of Preparation J, the compound of formula XXXVII is converted to the corresponding compound of formula XXXIII by reacting XXXVII with neat thionyl chloride. The reaction was stirred at a temperature between 0° C. to about 65° C., preferably about 55° C., for a time period between about 2 hours to about 12 hours, preferably about 8 hours.

In reaction 3 of Preparation J, the nitro compound of formula XXXVIII is converted to the corresponding amino compound of formula XXXIX according to the procedure described above in reaction 3 of Preparation A.

In reaction 1 of Preparation K, the compound of formula XXXIX is converted to the corresponding compound of formula XL according to the procedure described in reaction 1 of Preparation A.

In reaction 1 of Preparation L, the compound of formula XLI is converted to the corresponding compound of formula XLII according to the procedure described in reaction 1 of Preparation A.

In reaction 1 of Preparation M, the compound of formula XLIII is converted to the corresponding compound of formula XLIV according to the procedure described in reaction 1 of Preparation A.

In reaction 1 of Preparation N, the compound of formula XLV is converted to the corresponding compound of formula XLVI according to the procedure described in reaction 1 of Preparation A.

In reaction 1 of Preparation O, the compound of formula XLVII is converted to the corresponding compound of formula XLVIII according to the procedure described in reaction 1 of Preparation A.

In reaction 1 of Preparation P, the compound of formula XLIX is converted to the corresponding compound of formula L according to the procedure described in reaction 1 of Preparation A.

In reaction 1 of Scheme 1, the carboxylic acid compound of formula IV is converted to the corresponding acid chloride compound of formula III by reacting IV with oxalyl chloride in a polar aprotic solvent, such as methylene chloride. The reaction is stirred at a temperature between about 0° C. to about 40° C., preferably about 25° C., for a time period between about 2 hours to about 24 hours, preferably about 8 hours.

In reaction 2 of Scheme 1, the acid chloride compound of formula III is converted to the corresponding compound of formula II by reacting III with a compound of the formula

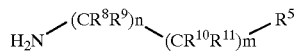

in the presence of a catalyst, such as pyridine, and a polar aprotic solvent, such as dimethylformamide. The reaction is stirred at a temperature between about 0° C. to about 25° C., preferably about 5° C., for a time period between about 1 hours to about 24 hours, preferably about 10 hours.

In reaction 1 of Scheme 2, the compound of formula VIII is converted to the corresponding carboxylic acid compound of formula VII by treating VIII with N-chlorosuccinimide followed by treatment with sodium hydroxide. The reaction is stirred at a temperature between about 0° C. to about 25° C., preferably about 20° C., for a time period about 1 hours to about 6 hours, preferably about 4 hours.

In reaction 2 of Scheme 2, the carboxylic acid compound of formula VII is converted to the corresponding acid chloride compound of formula VI according to the procedure described above in reaction 1 of Scheme 1.

In reaction 3 of Scheme 2, the acid chloride of formula VI is converted to the corresponding compound of formula V according to the procedure described in reaction 2 of Scheme 1.

In reaction 1 of Scheme 3, the carboxylic acid compound of formula XI is converted to the corresponding acid chloride compound of formula X according to the procedure described above in reaction 1 of Scheme 1.

In reaction 2 of Scheme 3, the acid chloride compound of formula X is converted to the corresponding compound of formula IX according to the procedure described above in reaction 2 of Scheme 1.

A patient in need of glycogen phosphorylase inhibition is a patient having a disease or condition in which glycogen phosphorylase plays a role in the disease of condition. Examples of patients in need of glycogen phoshphorylase inhibition include patients having diabetes (including Type I and Type II, impaired glucose tolerance, insulin resistance, and the diabetic complications, such a nephropathy, retinopathy, neuropathy and cataracts), hyperglycemia, hypercholesterolemia, hypertension, hyperinsulinemia, hyperlipidemia, atherosclerosis and tissue ischemia.

The characteristics of patients at risk of having atherosclerosis are well known to those skilled in the art and include, patients who have a family history of cardiovascular disease, including hypertension and atherosclerosis, obese patients, patient who exercise infrequently, patients with hypercholesterolemia, patients having high levels of low density lipoprotein (LDL), patients having low levels of high density lipoprotein (HDL), and the like.

Patients at risk of having myocardial ischemia and other tissue ischemias are also well known to those skilled in the art and include patients undergoing or having undergone surgery, trauma or great stress.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar—agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar—agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art.

The following paragraphs describe exemplary formulations, dosages etc. useful for non-human animals. The administration of a compound of the present invention can be effected orally or non-orally, for example by injection. An amount of a compound of the present invention is administered such that an effective dose is received, generally a daily dose which, when administered orally to an animal is usually between 0.01 and 100 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to about 500 ppm of the compound in the feed or water.

The preferred medicated swine, cattle, sheep and goat feed generally contain from about 1 to about 400 grams of active ingredient per ton of feed, the optimum amount for these animals usually being about 50 to about 300 grams per ton of feed.

The preferred poultry and domestic pet feeds usually contain about 1 to about 400 grams and preferably about 10 to about 400 grams of active ingredient per ton of feed.

For parenteral administration in animals, the compounds of the present invention may be prepared in the form of a paste or a pellet and administered as an implant, usually under the skin of the head or ear of the animal.

In general, parenteral administration involves injection of a sufficient amount of a compound of the present invention to provide the animal with about 0.01 to about 100 mg/kg/day of body weight of the active ingredient. The preferred dosage for poultry, swine, cattle, sheep, goats and domestic pets is in the range of from about 0.1 to about 50 mg/kg/day.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent in the level animal's body.

The term "salts" refers to inorganic and organic salts of compounds of the present invention. The salts can be prepared in situ during the final isolation and purification of a compound, or by separately reacting a purified compound in its free base form with a suitable organic or inorganic acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci,* 66: 1–19 (1977).

The term "prodrug" means compounds that are transformed in vivo to yield a compound of Formula I. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

In general the compounds of this invention can be made by processes which include processes analogous to those known in the chemical arts, particularly in light of the description contained herein.

In another aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the treatment of the diabetic complications, such as neuropathy, nephropathy, retinopathy or cataracts.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention or an other glycogen phosphorylase inhibitor in combination with an additional agent that can be used to treat diabetes and/or obesity. Preferred gylcogen phosphorylase inhibitors that are useful in combination with other agents useful to treat diabetes and/or obesity include those of Formula I. Additional preferred gylcogen phosphorylase inhibitors are disclsoed in PCT publications WO 96/39384 and WO 96/39385.

Representative agents that can be used to treat diabetes include insulin and insulin analogs: (e.g., LysPro insulin. inhaled formulations comprising insulin); GLP-1 (7-37) (insulinotropin) and GLP-1 (7-36)-NH$_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; glitazones: ciglitazone, pioglitazone, englitazone, troglitazone, darglitazone, rosiglitazone; PPAR-gamma agonists; RXR agonists: JTT-501, MCC-555, MX-6054, DRF2593,GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; β-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; lipid-lowering agents: benfluorex, atorvastatin; antiobesity agents: fenfluramine, orlistat, sibutramine; vanadate and vanadium complexes (e.g., Naglivan®) and peroxovanadium complexes; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antipolytic agents: nicotinic acid, acipimox, WAG 994; glucose transport stimulating agents: BM-130795; glucose synthase kinase inhibitors: lithium chloride, CT98014, CT98023; galanin receptor agonisnts; MTP inhibitors such as those disclosed in U.S. provisional patent application No. 60/164,803; growth hormone secretagogues such as those disclosed in PCT publication numbers WO 97/24369 and WO 98/58947; NPY antagonists: PD-160170, BW-383, BW1229, CGP-71683A, NGD 95-1, L-152804; Anorectic agents inlcuding 5-HT and 5-HT2C receptor antagonists and/or mimetics: dexfenfluramine, Prozac®, Zoloft®; CCK receptor agonists: SR-27897B; galanin receptor antagonists; MCR-4 antagonists: HP-228; leptin or mimetics: leptin; 11-beta-hydroxysteroid dehydrogenase type-I inhibitors; urocortin mimetics, CRF antagonists, and CRF binding proteins: RU-486, urocortin. Other anti-diabetic agents that can be used in combination with a glycogen phosphorylase inhibitor include ergoset and D-chiroinositol. Any combination of agents can be administered as described above.

In addition to the categories and compounds mentioned above, gylcogen phosphorylase inhibitors, preferably the compounds of the present invention, can be administered in combination with thyromimetic compounds, aldose reductase inhibitors, glucocorticoid receptor antagonists, NHE-1 inhibitors, or sorbitol dehydrogenase inhibitors, or combinations thereof, to treat or prevent diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, particularly myocardial ischemia.

It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones. U.S. Pat. Nos. 4,766,121; 4,826,876; 4,910,305; and 5,061,798 disclose certain thyroid hormone mimetics (thyromimetics), namely, 3,5-dibromo-3'-[6-oxo-3(1H)-pyridazinylmethyl]-thyronines. U.S. Pat. No. 5,284,971 discloses certain thyromimetic cholesterol lowering agents, namely, 4-(3-cyclohexyl-4-hydroxy or -methoxy phenylsulfonyl)-3,5 dibromo-phenylacetic compounds. U.S. Pat. Nos. 5,401,772; 5,654,468; and 5,569,674 disclose certain thyromimetics that are lipid lowering agents, namely, heteroacetic acid derivatives. In addition, certain oxamic acid derivatives of thyroid hormones are known in the art. For example, N. Yokoyama, et al. in an article published in the *Journal of Medicinal Chemistry*, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis X*) 1066: 321–324 (1995) and Z. F. Stephan et al. in an article published in *Atherosclerosis*, 126: 53–63 (1996), describe certain oxamic acid derivatives useful as lipid-lowering thyromimetic agents, yet devoid of undesirable cardiac activities. Other useful thyromimetics that can be used in combination with a glycogen phosphorylase inhibitor include CGS-26214.

Each of the thyromimetic compounds referenced above and other thyromimetic compounds can be used in combination with the compounds of the present invention to treat or prevent diabetes, insulin resistance, diabetic neuropathy, diabetic nephropathy, diabetic retinopathy, cataracts hyperglycemia, hypercholesterolemia, hypertension, hyperinsulinemia, hyperlipidemia, atherosclerosis, or tissue ischemia.

The compounds of the present invention can also be used in combination with aldose reductase inhibitors. Aldose reductase inhibitors constitute a class of compounds that have become widely known for their utility in preventing and treating conditions arising from complications of diabetes, such as diabetic neuropathy and nephropathy. Such compounds are well known to those skilled in the art and are readily identified by standard biological tests. For example, the aldose reductase inhibitors zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140 to Larson et al.

Aldose reductase inhibitors have been taught for use in lowering lipid levels in mammals. See, for example, U.S. Pat. No. 4,492,706 to Kallai-sanfacon and EP 0 310 931 A2 (Ethyl Corporation).

U.S. Pat. No. 5,064,830 to Going discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased)level of triglycerides in the blood, such diseases include cardiovascular disorders such as thrombosis, arteriosclerosis, myocardial infarction, and angina pectoris. A preferred aldose reductase inhibitor is 1-phthalazineacetic acid, 3,4-dihydro-4-oxo-3-[[5-trifluoromethyl)-2-benzothiazolyl]methyl]-, also known as zopolrestat.

The term aldose reductase inhibitor refers to compounds that inhibit the bioconversion of glucose to sorbitol, which is catalyzed by the enzyme aldose reductase.

Any aldose reductase inhibitor may be used in a combination with a compound of the present invention. Aldose reductase inhibition is readily determined by those skilled in the art according to standard assays (J. Malone, *Diabetes*, 29:861–864 (1980). "Red Cell Sorbitol, an Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose.

Accordingly, examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl]thioxomethyl]-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. No. 4,464,382, U.S. Pat. No. 4,791,126, U.S. Pat. No. 4,831,045);

4. 3-(4-bromo-2-fluorobenzyl)-7-Chloro-3,4-dihydro-2,4-dioxo-1 (2H)-quinazolineacetic acid (zenarestat, U.S. Pat. Nos. 4,734,419, and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. No. 5,270,342 and U.S. Pat. No. 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2-fluoro-spiro(9H-fluorene-9,4'-imidazolidine)2',5'-dione (U.S. Pat. No. 4,438,272);

13. 2,7-di-fluoro-spiro(9H-fluorene-9,4'-imidazolidine)2',5'-dione (U.S. Pat. No. 4,436,745, U.S. Pat. No. 4,438,272);

14. 2,7-di-fluoro-5-methoxy-spiro(9H-fluorene-9,4'-imidazolidine)2',5'-dione (U.S. Pat. No. 4,436,745, U.S. Pat. No. 4,438,272);

15. 7-fluoro-spiro(5H-indenol[1,2-b]pyridine-5,3'-pyrrolidine)2,5'-dione (U.S. Pat. No. 4,436,745, U.S. Pat. No. 4,438,272);

16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);

17. spiro[imidazolidine-4,5'(6H)-quinoline]2,5-dione-3'-chloro-7',8'-dihydro-7'-methyl-(5'-cis)(U.S. Pat. No. 5,066,659);

18. (2S,4S)-6-fluoro-2',5'-dioxospiro(chroman-4,4'-imidazolidine)-2-carboxamide (U.S. Pat. No. 5,447,946); and 19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula Ia below

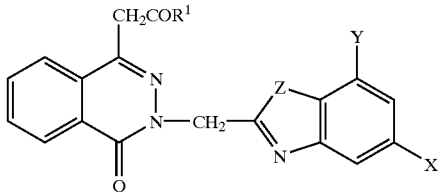

Ia or a pharmaceutically acceptable salt or prodrug thereof, wherein

Z is O or S;

$R^1$ is hydroxy or a group capable of being removed in vivo to produce a compound of formula I wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=$CF_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred. Procedures for making the aldose reducatase inhibitors of formula Ia can be found in PCT publication number WO 99/26659.

Each of the aldose reductase inhibitors referenced above and other aldose reductase inhibitors can be used in combination with the compounds of the present invention to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

The compounds of the present invention can also be used in combination with glucocorticoid receptor antagonists. The glucocorticoid receptor (GR) is present in glucocorticoid responsive cells Where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFK-B. Such interactions result in inhibition of API- and NFκ-B-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples or GR antagonists that can be used in combination with a compound of the present invention include compounds of formula Ib below:

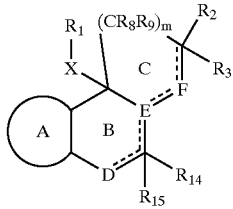

an isomer thereof, a prodrug of said compound or isomer, or a pharmaceutically acceptable salt of said compound, isomer or prodrug; wherein m is 1 or 2;

—represents an optional bond;

A is selected from the group consisting of

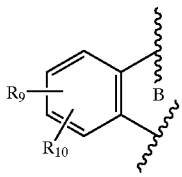 A-1

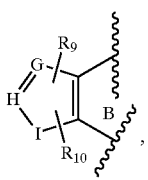 A-2

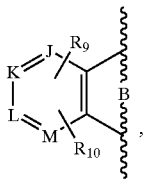 A-3

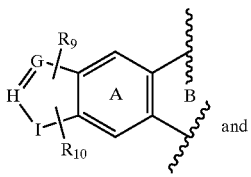 A-4 and

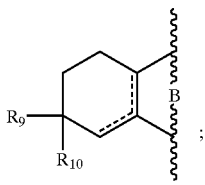 A-5

;

D is $CR_7$, $CR_7R_{16}$, N, $NR_7$ or O;

E is C, $CR_6$ or N;

F is $CR_4$, $CR_4R_5$ or O;

G, H and I together with 2 carbon atoms from the A-ring or 2 carbon atoms from the B-ring form a 5-membered heterocyclic ring comprising one or more N, O or S atoms; provided that there is at most one of O and S per ring;

J, K, L and M together with 2 carbon atoms from the B-ring forms a 6-membered heterocyclic ring comprising 1 or more N atoms;

X is a) absent, b) —$CH_2$—, c) —CH(OH)— or d) —C(O)—;

$R_1$ is a) —H, b) -Z-$CF_3$, c) —($C_1$–$C_6$)alkyl, d) —($C_2$–$C_6$)alkenyl, e) —($C_2$–$C_6$)alkynyl, f) —CHO, g) —CH=N—$OR_{12}$, h) -Z-C(O)$OR_{12}$, i) -Z-C(O)—$NR_{12}R_{13}$, j) -Z-C(O)—$NR_{12}$-Z-het, k) -Z-$NR_{12}R_{13}$, l) -Z-$NR_{12}$het, m) -Z-het, n) -Z-O-het, o) -Z-aryl', p) -Z-O-aryl', q) —CHOH-aryl' or r) —C(O)-aryl' wherein aryl' in substituents o) to r) is substituted independently with 0, 1 or 2 of the following: -Z-OH, -Z-$NR_{12}R_{13}$, -Z-$NR_{12}$-het, —C(O)$NR_{12}R_{13}$, —C(O)O($C_1$–$C_6$)alkyl, —C(O)OH, —C(O)-het, —$NR_{12}$—C(O)—($C_1$–$C_6$)alkyl, —$NR_{12}$—C(O)—($C_2$–$C_6$)alkenyl, —$NR_{12}$—C(O)—($C_2$–$C_6$)alkynyl, —$NR_{12}$—C(O)-Z-het, —CN, -Z-het, —O—($C_1$–$C_3$)alkyl-C(O)—$NR_{12}R_{13}$, —O—($C_1$–$C_3$)alkyl-C(O)O($C_1$–$C_6$)alkyl, —$NR_{12}$-Z-C(O)O($C_1$–$C_6$)alkyl, —N(Z-C(O)O($C_1$–$C_6$)alkyl)$_2$, —$NR_{12}$-Z-C(O)—$NR_{12}R_{13}$, -Z-$NR_{12}$—$SO_2$—$R_{13}$, —$NR_{12}$—$SO_2$-het, —C(O)H, -Z-$NR_{12}$-Z-O($C_1$–$C_6$)alkyl, -Z-$NR_{12}$-Z-$NR_{12}R_{13}$, -Z-$NR_{12}$—($C_3$–$C_6$)cycloalkyl, -Z-N(Z-O($C_1$–$C_6$)alkyl)$_2$, —$SO_2R_{12}$, —$SOR_{12}$, —$SR_{12}$, —$SO_2NR_{12}R_{13}$, —O—C(O)—($C_1$–$C_4$)alkyl, —O—$SO_2$13 ($C_1$–$C_4$)alkyl, -halo or —$CF_3$;

Z for each occurrence is independently a) —($C_0$–$C_6$)alkyl, b) —($C_2$–$C_6$)alkenyl or c) —($C_2$–$C_6$)alkynyl;

$R_2$ is a) —H, b) -halo, c) —OH, d) —($C_1$–$C_6$)alkyl substituted with 0 or 1 —OH, e) —$NR_{12}R_{13}$, f) -Z-C(O)O($C_1$–$C_6$)alkyl, g) -Z-C(O)$NR_{12}R_{13}$, h) —O—($C_1$–$C_6$)alkyl, i) -Z-O—C(O)—($C_1$–$C_6$)alkyl, j) -Z-O—($C_1$–$C_3$)alkyl-C(O)—$NR_{12}R_{13}$, k) -Z-O—($C_1$–$C_3$)alkyl-C(O)—O($C_1$–$C_6$)alkyl, l) —O—($C_2$–$C_6$)alkenyl, m) —O—($C_2$–$C_6$)alkynyl, n) —O-Z-het, o) —COOH, p) —C(OH)$R_{12}R_{13}$ or q) -Z-CN;

$R_3$ is a) —H, b) —($C_1$–$C_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 $R_y$, c) —($C_2$–$C_{10}$)alkenyl substituted with 0, 1 or 2 $R_y$, d) —($C_2$–$C_{10}$)alkynyl wherein 1 carbon atom, other than the connecting carbon atom, may optionally be replaced with 1 oxygen atom and wherein each carbon atom is substituted with 0, 1 or 2 $R_y$, e) —CH=C=$CH_2$, f) —CN, g) —($C_3$–$C_6$)cycloalkyl, h) -Z-aryl, i) -Z-het, j) —C(O)O($C_1$–$C_6$)alkyl, k) —O($C_1$–$C_6$)alkyl, l) -Z-S—$R_{12}$, m) -Z-S(O)—$R_{12}$, n) -Z-S(O)$_2$—$R_{12}$, o) —$CF_3$ p) —$NR_{12}$O—($C_1$–$C_6$)alkyl or q) —$CH_2OR_y$;

provided that one of $R_2$ and $R_3$ is absent when there is a double bond between $CR_2R_3$ (the 7 position) and the F moiety (the 8 position) of the C-ring;

$R_y$ for each occurrence is independently a) —OH, b) -halo, c) -Z-$CF_3$, d) -Z—CF($C_1$–$C_3$ alkyl)$_2$, e) —CN, f) —$NR_{12}R_{13}$, g) —($C_3$–$C_6$)cycloalkyl, h) —($C_3$–$C_6$)cycloalkenyl, i) —($C_0$–$C_3$)alkyl-aryl, j) -het or k) —$N_3$;

or $R_2$ and $R_3$ are taken together to form a) =$CHR_{11}$, b) =$NOR_{11}$, c) =O, d) =N—$NR_{12}$, e) =N—$NR_{12}$—C(O)—$R_{12}$, f) oxiranyl or g) 1,3-dioxolan-4-yl;

$R_4$ and $R_5$ for each occurrence are independently a) —H, b) —CN, c) —($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —O—($C_1$–$C_6$)alkyl substituted with 0 to 3 halo, g) —O—($C_2$–$C_6$)alkenyl substituted with 0 to 3 halo, h) —O—($C_2$–$C_6$)alkynyl substituted with 0 to 3 halo, i) halo, j) —OH, k) ($C_3$–$C_6$)cycloalkyl or l) ($C_3$–$C_6$)cycloalkenyl;

or $R_4$ and $R_5$ are taken together to form =O;

$R_6$ is a) —H, b) —CN, c) —($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo or f) —OH;

$R_7$ and $R_{16}$ for each occurrence are independently a) —H, b) -halo, c) —CN, d) —($C_1$–$C_6$)alkyl substituted with 0 to 3 halo, e) —($C_2$–$C_6$)alkenyl substituted with 0 to 3 halo or f) —($C_2$–$C_6$)alkynyl substituted with 0 to 3 halo; provided that $R_7$ is other than —CN or -halo when D is $NR_7$;

or $R_7$ and $R_{16}$ are taken together to form =O;

$R_8$, $R_9$, $R_{14}$ and $R_{15}$ for each occurrence are independently a) —H, b) -halo, c) ($C_1$–$C_6$)alkyl substituted with 0 to 3 halo, d) —($C_2$–$C_6$)alkenyl substituted with 0 to 3 halo, e) —($C_2$–$C_6$)alkynyl substituted with 0 to 3 halo, f) —CN, g) —($C_3$–$C_6$)cycloalkyl, h) —($C_3$–$C_6$)cycloalkenyl, i) —OH, j) —O—($C_1$–$C_6$)alkyl, k) —O—($C_1$–$C_6$)alkenyl, l) —O—($C_1$–$C_6$)alkynyl, m) —$NR_{12}R_{13}$, n) —C(O)$OR_{12}$ or o) —C(O)$NR_{12}R_{13}$;

or $R_8$ and $R_9$ are taken together on the C-ring to form =O; provided that when m is 2, only one set of $R_8$ and $R_9$ are taken together to form =O;

or $R_{14}$ and $R_{15}$ are taken together to form =O; provided that when $R_{14}$ and $R_{15}$ are taken together to form =O, D is other than $CR_7$ and E is other than C;

$R_{10}$ is a) —($C_1$–$C_{10}$)alkyl substituted with 0 to 3 substituents independently selected from -halo, —OH and —$N_3$, b) —($C_2$–$C_{10}$)alkenyl substituted with 0 to 3 substituents independently selected from -halo, —OH and —$N_3$, c) —($C_2$–$C_{10}$)alkynyl substituted with 0 to 3 substituents independently selected from -halo, —OH and —$N_3$, d) -halo, e) -Z-CN, f) —OH, g) -Z-het, h) -Z-$NR_{12}R_{13}$, i) -Z-C(O)-het, j) -Z-C(O)—($C_1$–$C_6$)alkyl, k) -Z-C(O)—$NR_{12}R_{13}$, l) -Z-C(O)—$NR_{12}$-Z-CN, m) -Z-C(O)—$NR_{12}$-Z-het, n) -Z-C(O)—$NR_{12}$-Z-aryl, o) -Z-C(O)—$NR_{12}$-Z-$NR_{12}R_{13}$, p) -Z-C(O)—$NR_{12}$-Z-O($C_1$–$C_6$)alkyl, q) —($C_1$–$C_6$)alkyl-C(O)OH, r) -Z-C(O)O($C_1$–$C_6$)alkyl, s) -Z-O—($C_0$–$C_6$)alkyl-het, t) -Z-O—($C_0$–$C_6$)alkyl-aryl, u) -Z-O—($C_1$–$C_6$)alkyl substituted with 0 to 2 $R_x$, v)-Z-O—($C_1$–$C_6$)alkyl-CH(O), w) -Z-O—($C_1$–$C_6$)alkyl-$NR_{12}$-het, x) -Z-O-Z-het-Z-het, y) -Z-O-Z-het-Z-$NR_{12}R_{13}$, z) -Z-O-Z-het-C(O)-het, a1) -Z-O-Z-C(O)-het, b1)-Z-O-Z-C(O)-het-het, c1)-Z-O-Z-C(O)—($C_1$–$C_6$)alkyl, d1) -Z-O-Z-C(S)—$NR_{12}R_{13}$, e1)-Z-O-Z-C(O)—$NR_{12}R_{13}$, f1) -Z-O-Z-($C_1$–$C_3$)alkyl-C(O)—$NR_{12}R_{13}$, g1)-Z-O-Z-C(O)—O($C_1$–$C_6$)alkyl, h1) -Z-O-Z-C(O)—OH, i1)-Z-O-Z-C(O)—$NR_{12}$—O($C_1$–$C_6$)alkyl, j1)-Z-O-Z-C(O)—$NR_{12}$—OH, k1) -Z-O-Z-C(O)—$NR_{12}$-Z-$NR_{12}R_{13}$, l1)-Z-O-Z-C(O)—$NR_{12}$-Z-het, m1) -Z-O-Z-C(O)—$NR_{12}$—$SO_2$—($C_1$–$C_6$)alkyl, n1)-Z-O-Z-C(=$NR_{12}$)($NR_{12}R_{13}$), o1) -Z-O-Z-C(=$NOR_{12}$)($NR_{12}R_{13}$), p1)-Z-$NR_{12}$—C(O)—O-Z-$NR_{12}R_{13}$, q1)-Z-S—C(O)—$NR_{12}R_{13}$, r1)-Z-O—$SO_2$—($C_1$–$C_6$)alkyl, s1)-Z-O—$SO_2$-aryl, t1)-Z-O—$SO_2$—$NR_{12}R_{13}$, u1) -Z-O—$SO_2$—$CF_3$, v1)-Z-$NR_{12}$C(O)$OR_{13}$ or w1)-Z-$NR_{12}$C(O)$R_{13}$;

or $R_9$ and $R_{10}$ are taken together on the moiety of formula A-5 to form a) =O or b) =$NOR_{12}$;

$R_{11}$ is a) —H, b) —($C_1$–$C_5$)alkyl, c) —($C_3$–$C_6$)cycloalkyl or d) —($C_0$–$C_3$)alkyl-aryl;

$R_{12}$ and $R_{13}$ for each occurrence are each independently a) —H, b) —($C_1$–$C_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —($C_2$–$C_6$)alkenyl substituted with 0 to 6 halo or d) —($C_1$–$C_6$)alkynyl wherein 1 carbon atom, other than the connecting carbon atom, may optionally be replaced with 1 oxygen atom and wherein each carbon atom is substituted with 0 to 6 halo;

or $R_{12}$ and $R_{13}$ are taken together with N to form het;

or $R_6$ and $R_{14}$ or $R_{15}$ are taken together to form 1,3-dioxolanyl;

aryl is a) phenyl substituted with 0 to 3 $R_x$, b) naphthyl substituted with 0 to 3 $R_x$ or c) biphenyl substituted with 0 to 3 $R_x$;

het is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 $R_x$;

$R_x$ for each occurrence is independently a) -halo, b) —OH, c) —($C_1$–$C_6$)alkyl, d) —($C_2$–$C_6$)alkenyl, e) —($C_2$–$C_6$)alkynyl, f) —O($C_1$–$C_6$)alkyl, g) —O($C_2$–$C_6$)alkenyl, h) —O($C_2$–$C_6$)alkynyl, i) —($C_0$–$C_6$)alkyl-$NR_{12}R_{13}$, j) —C(O)—$NR_{12}R_{13}$, k) -Z-$SO_2R_{12}$, l) -Z-$SOR_{12}$, m)-Z-$SR_{12}$, n) —$NR_{12}$—$SO_2R_{13}$, o) —$NR_{12}$—C(O)—$R_{13}$, p) —$NR_{12}$—$OR_{13}$, q) —$SO_2$—$NR_{12}R_{13}$, r) —CN, s) —$CF_3$, t) —C(O)(($C_1$–$C_6$)alkyl, u) =O, v) -Z-$SO_2$-phenyl or w) -Z-$SO_2$-het';

aryl' is phenyl, naphthyl or biphenyl;

het' is a 5-,6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:

1) X—$R_1$ is other than hydrogen or methyl;

2) when $R_9$ and $R_{10}$ are substituents on the A-ring, they are other than mono- or di-methoxy;

3) when $R_2$ and $R_3$ are taken together to form =$CHR_{11}$ or =O wherein $R_{11}$ is —O($C_1$–$C_6$)alkyl, then —X—$R_1$ is other than ($C_1$–$C_4$)alkyl;

4) when $R_2$ and $R_3$ taken together are C=O and $R_9$ is hydrogen on the A-ring; or when $R_2$ is hydroxy, $R_3$ is hydrogen and $R_9$ is hydrogen on the A-ring, then $R_{10}$ is other than —O—($C_1$–$C_6$)alkyl or —O—$CH_2$-phenyl at the 2-position of the A-ring;

5) when X—$R_1$ is ($C_1$–$C_4$)alkyl, ($C_2$–$C_4$)alkenyl or ($C_2$–$C_4$)alkynyl, $R_9$ and $R_{10}$ are other than mono-hydroxy or =O, including the diol form thereof, when taken together; and 6) when X is absent, $R_1$ is other than a moiety containing a heteroatom independently selected from N, O or S directly attached to the juncture of the B-ring and the C-ring. (See Published International Patent Application number WO00/66522)

Each of the glucocorticoid receptor antagonists referenced above and other glucocorticoid receptor antagonists can be used in combination with the compounds of the present invention to treat or prevent diabetes, hyperglycemia, hypercholesterolemia, hypertension, hyperinsulinemia, hyperlipidemia, atherosclerosis, or tissue ischemia.

The compounds of the present invention can also be used in combination with sorbitol dehydrogenase inhibitors. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

Each of the sorbitol dehydrogenase inhibitors referenced above and other sorbitol dehydrogenase inhibitors can be used in combination with the compounds of the present invention to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

The compounds of the present invention can also be used in combination with sodium-hydrogen exchanger type 1 (NHE-1) inhibitors. NHE-1 inhibitors can be used to reduce tissue damage resulting from ischemia. Of great concern is tissue damage that occurs as a result of ischemia in cardiac, brain, liver, kidney, lung, gut, skeletal muscle, spleen, pancreas, nerve, spinal cord, retina tissue, the vasculature, or intestinal tissue. NHE-1 inhibitors can also be administered to prevent perioperative myocardial ischemic injury.

Examples of NHE-1 inhibitors include a compound having the Formula Ic

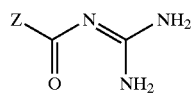

Formula Ic a prodrug thereof or a pharmaceutically acceptable salt of said compound or of said prodrug, wherein Z is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z is carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono- or di-substituted independently with hydroxy, ($C_1$–$C_4$)alkoxy, ($C_1$–$C_4$)alkylthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$)alkoxy, ($C_1$–$C_4$)alkoxycarbonyl, ($C_1$–$C_4$)alkyl, formyl, ($C_1$–$C_4$)alkanoyl, ($C_1$–$C_4$)alkanoyloxy, ($C_1$–$C_4$)alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, ($C_1$–$C_4$)alkylthio, ($C_1$–$C_4$)alkylsulfinyl, ($C_1$–$C_4$)alkylsulfonyl, mono-N- or di-N,N-($C_1$–$C_4$)alkylaminosulfonyl, ($C_2$–$C_4$)alkenyl, ($C_2$–$C_4$)alkynyl or ($C_5$–$C_7$)cycloalkenyl, wherein said ($C_1$–$C_4$)alkoxy, ($C_1$–$C_4$)alkyl, ($C_1$–$C_7$)alkanoyl, ($C_1$–$C_4$)alkylthio, mono-N- or di-N,N-($C_1$–$C_4$)alkylamino or ($C_3$–$C_7$)cycloalkyl $R^6$, $R^7$ and $R^8$ substituents are optionally mono-substituted independently with hydroxy, ($C_1$–$C_4$)alkoxycarbonyl, ($C_3$–$C_7$)cycloalkyl, ($C_1$–$C_4$)alkanoyl, ($C_1$–$C_4$)alkanoylamino, ($C_1$–$C_4$)alkanoyloxy, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, nitro, ($C_1$–$C_4$)alkylthio, ($C_1$–$C_4$)alkylsulfinyl, ($C_1$–$C_4$)alkylsulfonyl or mono-N- or di-N,N-($C_1$–$C_4$)alkylaminosulfonyl or optionally substituted with one to nine fluorines. (See PCT patent applciation number PCT/IB99/00206)

Each of the NHE-1 inhibitors referenced above and other NHE-1 inhibitors can be used in combination with the compounds of the present invention to treat or prevent diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

The examples presented below are intended to illustrate particular embodiments of the invention, and are not intended to limit the scope of the specification, including the claims, in any manner. All patents, patent applications, and other references cited in this application are hereby incorporated by reference.

Biological Protocols

The utility of the compounds of the present invention as medical agents in the treatment or prevention of diseases (such as are detailed herein) in animals, particularly mammals (e.g. humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in animals, particularly mammals, including humans, for the treatment of such diseases.

Glycogen Phosphorylase Production and Assays

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP cDNAs (obtained as described in Newgard et al., *Proc. Natl. Acad. Sci.*, 83: 8132–8136 (1986), and Newgard et al., *Proc. Natl. Acad. Sci.*, 263: 3850–3857 (1988), respectively) and HMGP cDNAs (obtained by screening a Stratagene (Stratagene Cloning Systems, La Jolla, Calif.) human muscle cDNA library with a polymerase chain reaction (PCR)-generated cDNA fragment based on information and methodology reported for isolation of the human skeletal muscle glycogen phosphorylase gene and partial cDNA sequence by Kubisch et al., Center for Molecular Neurobiology, University of Hamburg, Martinistrasse 85, Hamburg, 20246 Germany; Genbank (National Center for Biotechnology Information, National Institutes of Health, USA) Accession Numbers U94774, U94775, U94776 and U94777, submitted Mar. 20, 1997; Burke et al., *Proteins*, 2:177–187 (1987); and Hwang et al., *Eur. J. Biochem.*, 152: 267–274 (1985)) are expressed from plasmid pKK233-2 (Pharmacia Biotech. Inc., Piscataway, N.J.) in *E. coli* strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/l pyridoxine and 600 mg/L $MnCl_2$ and grown at 37° C. to a cell density of $OD_{550}=1.0$. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (*J. Biol. Chem.* 270:13748–13756 (1995)). The method described by Crerar, et al. (*J. Biol. Chem.*, 270:13748–13756 (1995)) for the expression of HBGP is as follows: the HBGP cDNA can be expressed from plasmid pTACTAC in *E. coli* strain 25A6. The strain is inoculated into LB medium (consisting of 10 g tryptone, 5 g yeast extract, 5 g NaCl, and 1 ml 1N NaOH per liter) plus 50 mg/L ampicillin and grown overnight, then resuspended in fresh LB medium plus 50 mg/L ampicillin, and reinoculated into a 40× volume of LB/amp media containing 250 μM isopropyl-1-thio-β-D-galactoside (IPTG), 0.5 mM pyridoxine and 3 mM $MnCl_2$ and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium (Sf-900 II serum free medium, Gibco BRL, Life Technologies, Grand Island, N.Y.) are infected at an moi of 0.5 and at a cell density of $2\times10^6$ cells/ml. After growth for 72 hours at 27° C., cells are centrifuged, and the cell pellets frozen at −70° C. until needed for purification.

Purification of Glycogen Phosphorylase Expressed in *E. coli*

The *E. coli* cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 μg/ml | Pepstatin A |
| 0.5 μg/ml | Leupeptin |
| 0.2 mM | phenylmethylsulfonyl fluoride (PMSF), and |
| 0.5 mM | EDTA, | lysed by pretreatment with 200 μg/ml lysozyme and 3 μg/ml DNAase followed by sonication in 250 ml batches for 5×1.5 minutes on ice using a Branson Model 450 ultrasonic cell disrupter (Branson Sonic Power Co., Danbury Conn.). The *E. coli* cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. *Journal of Chromatography* 584: 77–84 (1992)). Five hundred ml of the filtered soluble fraction of cell lysates (prepared from approximately 160–250 g of original cell pellet) are loaded onto a 130 ml column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 (equilibration buffer). The column is washed with equilibration buffer until the $A_{280}$ returns to baseline. The sample is then eluted from the column with the same buffer containing 100 mM imidazole to remove the bound GP and other bound proteins. Fractions containing the GP activity are pooled (approximately 600 ml), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/ml and 0.7 μg/ml concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice and subjected to a second chromatographic step (below) if necessary.

5'-AMP-Sepharose Chromatography

The desalted pooled GP sample (approximately 600 mL) is next mixed with 70 ml of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity described below and visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl2, plus the following protease inhibitors:

| | |
|---|---|
| 0.7 μg/ml | Pepstatin A |
| 0.5 μg/ml | Leupeptin |
| 0.2 mM | phenylmethylsulfonyl fluoride (PMSF), and |
| 0.5 mM | EDTA, | lysed by pretreatment with 3 μg/ml DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, as described below, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 µg/ml leupeptin and 1.0 µg/ml pepstatin A. The fraction is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis-(2-hydroxyethyl)-2-aminoethanesulfonic acid (BES), 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in E. coli strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the follow procedure.

GP Reaction with Immobilized Phosphorylase Kinase

Phosphorylase kinase (Sigma Chemical Company, St. Louis, Mo.) is immobilized on Affi-Gel® 10 (BioRad Corp., Melvile, N.Y.) as per the manufacturer's instructions. In brief, the phosphorylase kinase enzyme (10 mg) is incubated with washed Affi-Gel® beads (1 ml) in 2.5 ml of 100 mM HEPES and 80 mM $CaCl_2$ at pH 7.4 for 4 hours at 4° C. The Affi-Gel® beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel® immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive GPb obtained from 5'-AMP-Sepharose chromatography above (from E. coli) or the mixture of GPa and GPb obtained from IMAC above (from Sf9 cells) is diluted 1:10 with the kinase assay buffer then mixed with the aforementioned phosphorylase kinase enzyme immobilized on the Affi-Gel® beads. NaATP is added to 5 mM and $MgCl_2$ to 6 mM. The resulting mixture is mixed gently at 25° C. for 30 to 60 minutes. The activated sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total } HLGPa = \frac{HLGP \text{ activity} - AMP}{HLGP \text{ activity} + AMP}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to E. coli derived GPa and GPb standards that are run in parallel on the same gels as the experimental samples.

B) GPa Activity Assay

The disease/condition treating/preventing activities described herein of the compounds of the present invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. Clinical Chemistry 23: 1711–1717 (1977)] modified as follows: 1 to 100 µg GPa, 10 units phosphoglucomutase and 15 units glucose-6-phosphate dehydrogenase (Boehringer Mannheim Biochemicals, Indianapolis, Ind.) are diluted to 1 mL in Buffer D (pH 7.2, 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol). Twenty µl of this stock is added to 80 µl of Buffer D containing 0.47 mg/mL glycogen, 9.4 mM glucose, 0.63 mM of the oxidized form of nicotinamide adenine dinucleotide phosphate (NADP+). The compound to be tested is added as 5 µl of solution in 14% dimethylsulfoxide (DMSO) prior to the addition of the enzymes. The basal rate of GPa enzyme activity in the absence of inhibitors, e.g., a compound of this invention, is determined by adding 5 µl of 14% DMSO and a fully-inhibited rate of GPa enzyme activity is obtained by adding 20 µl of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B., *Can. J. Biochem.* 48: 746–754 (1970)] modified as follows: 1 to 100 ug GPa is diluted to 1 ml in Buffer E (pH 7.2, 50 mM HEPES, 100 mM KCl, 2.5 mM EGTA, 2.5 mM $MgCl_2$ and 0.5 mM dithiothreitol). Twenty µl of this stock is added to 80 µl of Buffer E with 1.25 mg/ml glycogen, 9.4 mM glucose, and 0.63 mM glucose-1-phosphate. The compound to be tested is added as 5 µl of solution in 14% DMSO prior to the addition of the enzyme. The basal rate of GPa enzyme activity in the absence of added inhibitors, e.g., a compound of this invention, is determined by adding 5 µl, of 14% DMSO and a fully-inhibited rate of GPa enzyme activity is obtained by adding 20 µL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. *Anal. Biochem.* 100: 95–97 (1979)] modified as follows: 150 µl of 10 mg/ml ammonium molybdate, 0.38 mg/ml malachite green in 1 N HCl is added to 100 µl of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

The compounds of this invention are readily adapted to clinical use as hypoglycemic agents. The hypoglycemic activity of the compounds of this invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Since the concentration of glucose in blood is closely related to the development of diabetic disorders, the compounds of the present invention, by virtue of their hypoglycemic action, prevent, arrest and/or regress diabetic disorders.

Five to eight week old male C57BL/6J-ob/ob mice (obtained from Jackson Laboratory, Bar Harbor, Me.) are housed five per cage under standard animal care practices. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water; or 3) neat PEG 400 without pH adjustment; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™Glucose-UV Test reagent system (Abbott Laboratories, Irving, Tex.) (a modification of the method of Richterich and Dauwalder, *Schweizerische Medizinische Wochenschrift*, 101: 860 (1971)) (hexokinase method) using a 100 mg/dl standard. Plasma glucose is then calculated by the equation:

$$\text{Plasma glucose (mg/dl)} = \text{Sample value} \times 8.14$$

where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

The compounds of the present invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of this invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of this invention, by virtue of their hypoinsulinemic action, prevent, arrest and/or regress hypertension.

Since the concentration of triglycerides in blood contributes to the overall levels of blood lipids, the compounds of this invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either (1) 10% DMSO/

0.1% Pluronic® P105 Block Copolymer Surfactant (BASF Corporation, Parsippany, N.J.) in 0.1% saline without pH adjustment or (2) 0.25% w/v methylcellulose in water without pH adjustment. Alternatively, the compound to be tested can be adminsitrered by oral gavage dissolved in or in suspension in neat PEG 400. Single daily dosing (s.i.d.) or twice daily dosing (b.i.d.) is maintained for 1 to, for example, 15 days. Control mice receive the 10% DMSO/ 0.1% Pluronic® P105 in 0.1% saline without pH adjustment or the 0.25% w/v methylcellulose in water without pH adjustment, or the neat PEG 400 without pH adjustment.

Three hours after the last dose is administered, the animals are sacrificed by decapitation and trunk blood is collected into 0.5 ml serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/volume with a 1 TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The inter assay coefficient of variation is $\leq 10\%$. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from Amano International Enzyme Co., Inc., as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations, Serum insulin ($\mu$U/ml)=Sample value×2

Serum triglycerides (mg/dl)=Sample value×2

Serum total cholesterol (mg/dl)=Sample value×2

Serum free fatty acid ($\mu$Eq/l)=Sample value×2 where 2 is the dilution factor.

The animals dosed with vehicle maintain substantially unchanged, elevated serum insulin (e.g., 275 $\mu$U/ml), serum triglycerides (e.g., 235 mg/dl), serum free fatty acid (1500 mEq/ml) and serum total cholesterol (e.g., 190 mg/dl) levels, while animals treated with compounds of the present invention generally display reduced serum insulin, triglycerides, free fatty acid and total cholesterol levels. The serum insulin, triglycerides, free fatty acid and total cholesterol lowering activity of the test compounds are determined by statistical analysis (unpaired t-test) of the mean serum insulin, triglycerides, or total cholesterol concentration between the test compound group and the vehicle-treated control group.

The present invention is illustrated by the following examples, but it is not limited to the details thereof.

PREPARATIONS

Preparation 1

Methyl 2,3-dihydroxy Benzoate

A mixture of 92.472 g (0.6 mol) of 2,3-dihydroxybenzoic acid (FW 154.12; Aldrich cat.# 12,620-9; RSO # 9449), 100 mL of anhydrous methanol and 3 mL of concentrated sulfuric acid was heated to reflux for 36 hrs. After cooling down, reaction mixture was concentrated down to approximately ⅓ of its volume and poured on ice. A precipitate that formed was washed thoroughly with cold water, filtered off and dried in the desiccator over calcium sulfate. Yield 98.4 g of off-white solid (98%). This was used without further purification.

LC MS: AP$^+$ 169, AP$^-$ 167.

Preparation 2

3,4-Dihydro-2H-benzo[b][1,4]dioxepine-6-carboxylic acid methyl ester

A flame dried 1 L-flask was charged with 82.7 grams (0.6 mol) of finely ground and flame dried potassium carbonate and 200 mL of absolute dimethylformamide and kept under nitrogen gas. This reaction mixture was then stirred and warmed up to 40° C. A 47.23 g (29.7 mL, 0.3 mol) of 1-bromo-3-Chloropropane was then added to the reaction flask rapidly followed by 50.445 g (0.3 mol) of methyl 2,3-dihydroxy benzoate (C-2). The reaction was then heated to 100° C. (110° C. was the temp. of an oil bath) under reflux condenser for 6 hrs. After cooling, the reaction was filtered to remove all the solids, solids washed with 50 mL of DMF and filtrate concentrated on the rotary evaporator. The residue was then partitioned between water and ethyl acetate. The organic layer was then washed with 200 mL of 1N NaOH to remove any starting material, followed by 5% HCl, 5% NaHCO$_3$, water and brine. Dried with magnesium sulfate. Filtered, stripped. Crude 55.63 grams. The product was then purified by the means of flash chromatography (400 g of silica gel, 20% AcOEt/hexanes). Collected 38.54 g (62%) as clear oil.

LC MS: AP$^+$ 209, AP$^-$ 207.

Preparation 3

8-Nitro-3,4-dihydro-2H-benzo[b][1,4]dioxepine-6-carboxylic acid methyl ester (C-4) and 9-Nitro-3,4-dihydro-2H-benzo[b][1,4]dioxepine-6-carboxylic acid methyl ester (C-5)

A 17.15 g (0.0825 mol) of (3,4-Dihydro-2H-benzo[b][1,4]dioxepine-6-carboxylic acid methyl ester; C-3) was dissolved in a mixture of 65 mL of glacial acetic acid and 65 mL of acetic anhydride. The reaction mixture was heated to 45° C. and treated with a solution of 12 mL of 90% HNO$_3$ (fuming) in 12 mL of glacial acetic acid dropwise. The reaction was then heated to 45–50° C. for 4 hours under reflux condenser. When cooled down, the reaction mixture was poured on a mix of ice and water and the yellow precipitate collected on a filter. Washed with water and dried on air. Crude 17.6 grams (this product was a mixture of the meta- (about 30%) and para-nitration (about 60%) products. This was used without further purification.
LC MS: AP⁻ 253 (for the mixture)

Preparation 4: Purification of Intermediate C-5 and Preparation of Acid Intermediate C-6

Nitro-3,4-dihydro-2H-benzo[b][1,4]dioxepine-6-carboxylic acid methyl ester (C-5): 8-Nitro-3,4-dihydro-2H-benzo[b][1,4]dioxepine-6-carboxylic acid (C-6)

The solid collected from Preparation 3 (17.6 g) was combined with 2.8 g of sodium hydroxide in a 1:4 mixture of THF and water. The reaction mixture was stirred at room temperature overnight and the solid that filled the flask collected on a filter to yield 8.6 g of un-hydrolyzed ester C-6 (LCMS: AP⁻ 253). The filtrate was acidified with concentrated HCl and the yellow solid collected on a filter to yeild 7.04 g of carboxylic acid of C-6. Recrystallized from ethyl acetate to give C-6 as yellow needles (5.96 g). LC MS: AP⁻ 238.

Preparation 5

8-Amino-3,4-dihydro-2H-benzo[b][1,4]dioxepine-6-carboxylic acid methyl ester

A mixture of 8-nitro-3,4-dihydro-2H-benzo[b][1,4]dioxepine-6-carboxylic acid methyl ester (0.58 g), SnCl₂ (2.17 g) and ethanol was refluxed at 70° C. for 2 hours. The reaction was poured over ice and the resulting aqueous solution treated with 5% NaHCO₃ (pH 7–8) and extracted with EtOAc. The organic phase was dried with MgSO₄ and solvent removed in vacuo to yield 0.318 g of product which was used directly in the next reaction. MS: M⁺ 224.

Preparation 6: Intermediates

To a cold CH₂Cl₂ (2.3 mL) solution of 8-nitro-3,4-dihydro-2H-benzo[b][1,4]dioxepine-6-carboxylic acid (C-6; 2.31 g) was added 10 mL of a 1M (COCl)₂ solution in methylene chloride. To that mixture was then added 4 drops of DMF. The reaction was stirred at room temperature for 2 hours and used with out further purification in the following protocols.

To 1.0 mmol of the amine was added 1.0 mmol of the above prepared acid chloride in dry CH₂Cl₂ containing one drop of DMF. The reaction was stirred for 2 hours and then diluted with 6N HCl and partitioned between EtOAc and water. The organic phase was separated, dried with MgSO₄ and solvent removed to yield the product.

According to the above procedure, the following nitro amides were analogously prepared:

8-Nitro-3,4-dihydro-2H-benzo[b][1,4]dioxepine-6-carboxylic acid (2-hydroxy-ethyl)-amide
8-Nitro-3,4-dihydro-2H-benzo[b][1,4]dioxepine-6-carboxylic acid dimethyl amide.
Morpholin-4-yl-(8-nitro-3,4-dihydro-2H-benzo[b][1,4]dioxepin-6-yl)-methanone
(8-Nitro-3,4-dihydro-2H-benzo[b][1,4]dioxepin-6-yl)-piperidin-1-yl-methanone
(8-Nitro-3,4-dihydro-2H-benzo[b][1,4]dioxepin-6-yl)-thiomorpholin-4-yl-methanone
8-Nitro-3,4-dihydro-2H-benzo[b][1,4]dioxepine-6-carboxylic acid diethylamide
(8-Nitro-3,4-dihydro-2H-benzo[b][1,4]dioxepin-6-yl)-pyrrolidin-1-yl-methanone
(3,4-Dihydroxy-pyrrolidin-1-yl)-(8-nitro-3,4-dihydro-2H-benzo[b][1,4]dioxepin-6-yl)-methanone
(4-Methyl-piperazin-1-yl)-(8-nitro-3,4-dihydro-2H-benzo[b][1,4]dioxepin-6-yl)-methanone
8-Nitro-3,4-dihydro-2H-benzo[b][1,4]dioxepine-6-carboxylic acid (2-methoxy-ethyl)-amide
8-Nitro-3,4-dihydro-2H-benzo[b][1,4]dioxepine-6-carboxylic acid (2-hydroxy-ethyl)-amide Preparation 7

The following amines were further prepared.
8-Amino-3,4-dihydro-2H-benzo[b][1,4]dioxepine-6-carboxylic acid (2-hydroxy-ethyl)-amide
8-Amino-3,4-dihydro-2H-benzo[b][1,4]dioxepine-6-carboxylic acid dimethyl amide.
Morpholin-4-yl-(8-amino-3,4-dihydro-2H-benzo[b][1,4]dioxepin-6-yl)-methanone
(8-Amino-3,4-dihydro-2H-benzo[b][1,4]dioxepin-6-yl)-piperidin-1-yl-methanone
(8-Amino-3,4-dihydro-2H-benzo[b][1,4]dioxepin-6-yl)-thiomorpholin-4-yl-methanone
8-Amino-3,4-dihydro-2H-benzo[b][1,4]dioxepine-6-carboxylic acid diethylamide
(8-Amino-3,4-dihydro-2H-benzo[b][1,4]dioxepin-6-yl)-pyrrolidin-1-yl-methanone
(3,4-Dihydroxy-pyrrolidin-1-yl)-(8-amino-3,4-dihydro-2H-benzo[b][1,4]dioxepin-6-yl)-methanone
(4-Methyl-piperazin-1-yl)-(8-amino-3,4-dihydro-2H-benzo[b][1,4]dioxepin-6-yl)-methanone
8-Amino-3,4-dihydro-2H-benzo[b][1,4]dioxepine-6-carboxylic acid (2-methoxy-ethyl)-amide
8-Amino-3,4-dihydro-2H-benzo[b][1,4]dioxepine-6-carboxylic acid (2-hydroxy-ethyl)-amide Preparation 8

8-Nitro-3,4-dihydro-2H-benzo[b][1,4]dioxepin-6-yl)-methanol

A flame dried flask in an inert atmosphere of dry nitrogen was charged with 5.96 g (0.025 mol) of 8-nitro-3,4-dihydro-2H-benzo[b][1,4]dioxepine-6-carboxylic acid and 10 mL of anhydrous THF. The reaction mixture was cooled in an ice bath and 25 mL of 1 M borane.tetrahydrofurane complex (0.025 mol) was added portion-wise via syringe. The reaction was then stirred at room temperature for 2 hrs and checked on TLC (only about 60% of conversion). Another 20 mL of 1 M BH₃.THF (0.02 mol) was then added and reaction stirred for additional 2 hrs at room temperature. After this time, the reaction mixture was carefully quenched with 10 mL of saturated ammonium chloride and partitioned between ethyl acetate and water. The organic phase washed with 5% NaHCO₃, water, brine, dried with sodium sulfate, filtered and concentrated in vacuo. 4.78 g of crude material was collected which was recrystallized from boiling toluene. 3.46 g (62%) of pure material was obtained as yellow needles.
LC MS AP⁺ 210 (loss of water), AP⁻ 225.

Preparation 9

(8-Amino-3,4-dihydro-2H-benzo[b][1,4]dioxepin-6-yl)-methanol 2.25 g (0.01 mol) of nitro benzyl alcohol compound was dissolved in a mixture of 45 mL of methanol and 45 mL of THF. A solid ammonium formate was then added (3.18 g, 0.05 mol, 5 equivalents) followed by the careful addition of 455 mg of 10% palladium on carbon. The reaction mixture was then stirred very slowly at room temperature under reflux condenser. Once it starts, the reaction was rapid and exothermic. After about 1 hour the evolution of hydrogen gas ceased and reaction was checked on TLC (more polar product formation, reaction was dome after this time). The crude reaction was then filtered thru celite, the filtrate diluted with four times of its volume of diethyl ether. The white precipitate that formed was filtered off and dried in vacuo. 1.403 g (72%) of off-white solid was collected.

LC MS: AP+ 196

Preparation 10

(2-Nitro-7,8-dihydro-6H-5-oxa-9-aza-benzocyclohepten-9-yl)-acetic acid ethyl ester Powdered and flame dried potassium carbonate (1.52 g, 11 mmol, 1.1 eq.) was placed in a round bottom flask together with 60 mL of anhydrous dimethylformamide and kept under inert atmosphere. 2-Nitro-6,7,8,9-tetrahydro-5-oxa-9-aza-benzocycloheptene (1.942 g, 10 mmol, 1 eq.) was dissolved in 20 mL of anhydrous DMF and added to the reaction mixture. The reaction was heated to 120° C. under reflux condenser for 1 hour and then solution of ethyl bromoacetate (3.34 g, 2.22 mL, 20 mmol, 2 eq.) in 5 mL of dry DMF was added dropwise to the hot solution. The reaction mixture was then heated to 120° C. for an additional 12 hours. When cooled, the DMF was removed on the rotary evaporator, and diluted with 100 mL of water. The aqueous phase was washed (3×) with 50 mL portions of methylene chloride. The methylene chloride extracts were combined and washed with water and brine and dried over magnesium sulfate. Crude material (3.018 g) was chromatographed on a large Biotage column in 20% ethyl acetate/hexanes. 1.38 g (50% yield) of pure material (bright yellow crystalline powder) was collected. LC MS: AP+281, AP–280.

Preparation 11

(2-Amino-7,8-dihydro-6H-5-oxa-9-aza-benzocyclohepten-9-yl)-acetic acid ethyl ester 2-Nitro-7,8-dihydro-6H-5-oxa-9-aza-benzocyclohepten-9-yl)-acetic acid ethyl ester (841 mg, 3 mmol, 1.0 eq.) was dissolved in 15 mL MeOH and 15 mL THF. Eighty mg of 10% Pd/C was carefully added under nitrogen together with of ammonium formate (946 mg, 15 mmol, 5 eq.). The stoppered reaction mixture was stirred at room temperature for two hours. The reaction mixture was then diluted with 150 mL of diethyl ether, filtered through celite and concentrated. The product (oil, 94 mg (75%)) was homogenous by TLC (100% AcOEt, Rf=0.4) and was used without further purification in the subsequent coupling reactions. LC MS: AP+ 251.

EXAMPLES

Example 1

5-Chloro-1H-Indole-2-carboxylic acid (3,4-dihydro-2H-benzo[b][1,4]dioxepin-7-yl)-amide 1. Reagent Preparations:

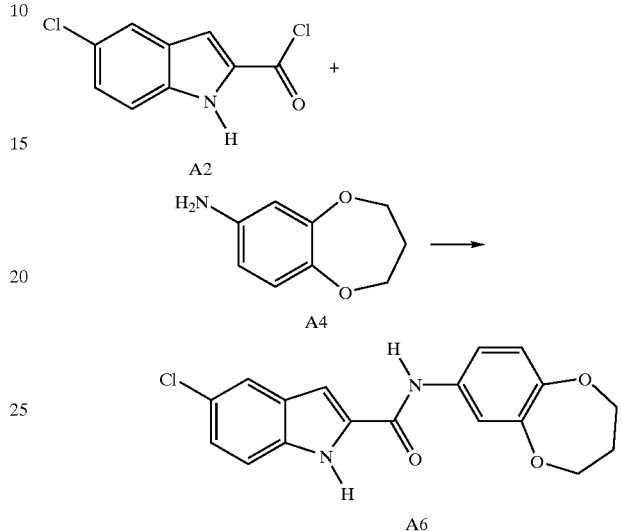

Preparation of a 1M (COCl$_2$)$_2$ solution in CH$_2$Cl$_2$.
  a. Added 25 g of (COCl$_2$)$_2$ to 100 mL of CH$_2$Cl$_2$.
  b. Diluted the solution to 200 mL total volume.
2. Preparation fo 0.5 M acid chloride (5-Chloro-1H-Indole-2-carboxylic acid (3,4-dihydro-2H-benzo[b][1,4]dioxepin-7-yl)-amide), in CH$_2$Cl$_2$.
  a. Added 1M (COCl$_2$)$_2$/CH$_2$Cl$_2$ (14 mL) to a slurry of 5-Chloro-1H-Indole-2-carboxylic acid (2.09 g) in CH$_2$Cl$_2$ (10 mL), with ice bath cooling.
  b. Added DMF (0.4 mL) over 5 minutes.
  c. Stirred at room temperature for 2 hours
  d. Filtered
  e. Diluted to 26 mL with CH$_2$Cl$_2$.
3. Aryl amines (100 uM, each) were weighed into ½ dram septum vials, numbered A1 . . . H6 using a standard 96 well micro titer format.
4. Pyridine (100 uL) was aded to each amine.
5. DMF (200 mL) was added to each reaction.
6. The above 0.5 M acid chloride solution (0.24 mL, 120 uM) was added to each.
7. Reactions were shaken over night.

Purification:

1. Solvent was removed by a ntirogen stream at 50° C.
2. Reaction residues were dissolved in DMSO (500 uL) and filtered.
3. The reaction filtrates were cloned for LCMS.
4. The filtrates which showed a parent ion were purified by reverse phase HPLC to afford pure product.

Alternately, each reaction could be prepared in a single reaction vessel under standard conditions described above and using the same protocol described above.

Example 2

8-[(5-Chloro-1H-indole-2-carbonyl)amino]-3,4-dihydro-2H-benzo[b][1,4]dioxepine-6-carboxylic acid methyl ester 8-Amino-3,4-dihydro-2H-benzo[b][1,4]dioxepine-6-carboxylic acid methyl ester (0.300 g), 5-Chloro-1H-Indole-2-carboxylic acid (0.263 g), BOP (0.594), TEA (0.377 mL) and DMF (3.0 mL) were mixed together and stirred for 4 hours. The reaction was diluted with water and the resulting filtrate filtered. The resulting solid was tritriated with EtOAc, rinished with the same and purified by flash chromatography (silica gel; 25% EtOAc/hexane) to yield 122 mg of the product. MS PDS: $M^+$ 401/403

Example 3

8-[(5-Chloro-1H-indole-2-carbonyl)amino]-3,4-dihydro-2H-benzo[b][1,4]dioxepine-6-carboxylic acid 8-[(5-Chloro-1H-indole-2-carbonyl)amino]-3,4-dihydro-2H-benzo[b][1,4]dioxepine-6-carboxylic acid methyl ester (120 mg) was dissolved in a mixture of THF/water and 0.3 mL of 1N KOH. The reaction was stirred at room temperature overnight, made acidic with 1N HCl and then extracted with EtOAc. The organic extract was washed with water, brine and dried with MgSO4. This afforded 35 mg of product. MS POS: $M^+$ 387/389.

Example 4

9-Amino-3,4-dihydro-2H-benzo[b][1,4]dioxepine-6-carboxylic acid methyl ester To a mixture of 9-nitro-3,4-dihydro-2H-benzo[b][1,4]dioxepine-6-carboxylic acid methyl ester (C-5; 2.53 g) and Pd/C (450 mg) suspended in 90 mL of a 1/1 mixture of THF/CH$_3$OH was added HCO$_2$HN$_4$ (3.153 g) and the resulting reaciton heated to 70° C. for 30 minutes. The reaction was diluted with 900 mL of diethyl ether. The resulting solution was filtered through celite and the organic solvent removed in vacuo to yield 2.152 g of white crystalline soldid. $AP^+$ 192 (—OCH$_3$).

Example 5

9-[(1H-indole-2-carbonyl)amino]-3,4-dihydro-2H-benzo[b][1,4]dioxepine-6-carboxylic acid methyl ester

LCMS: $AP^+$ 365

Example 6

9-[(5-Fluoro-1H-indole-2-carbonyl)amino]-3,4-dihydro-2H-benzo[b][1,4]dioxepine-6-carboxylic acid methyl ester

LCMS: $AP^+$ 385

Example 7

9-[(5-Chloro-1H-indole-2-carbonyl)amino]-3,4-dihydro-2H-benzo[b][1,4]dioxepine-6-carboxylic acid methyl ester

LCMS: $AP^+$ 401

Example 8

9-[(1H-indole-2-carbonyl)amino]-3,4-dihydro-2H-benzo[b][1,4]dioxepine-6-carboxylic acid 9-[(1H-indole-2-carbonyl)amino]-3,4-dihydro-2H-benzo[b][1,4]dioxepine-6-carboxylic acid methyl ester (E-2; R=H; 50 mg) was combined with 1 mL of THF and 1 mL of 1M NaOH and the reaction stirred for 4 days at room temperature. The solid was collected on a filter to yield 23 mg of a solid. LCMS: $AP^+$ 353.

Example 9

9-[(5-Fluoro-1H-indole-2-carbonyl)amino]-3,4-dihydro-2H-benzo[b][1,4]dioxepine-6-carboxylic acid

LCMS: $AP^+$ 371.

Example 10

9-[(5-Chloro-1H-indole-2-carbonyl)amino]-3,4-dihydro-2H-benzo[b][1,4]dioxepine-6-carboxylic acid

LCMS: $AP^+$ 387/389.

Example 11

The following compounds were further prepared.

5-Chloro-1H-indole-2-carboxylic acid (9-carbamoyl-3,4-dihydro-2H-benzo[b][1,4]dioxepin-7-yl)-amide 5-Chloro-1H-indole-2-carboxylic acid [9-(pyrrolidine-1-carbonyl)-3,4-dihydro-2H-benzo[b][1,4]dioxepin-7-yl]-amide 5-Chloro-1H-indole-2-carboxylic acid (9-dimethylcarbamoyl-3,4-dihydro-2H-benzo[b][1,4]dioxepin-7-yl)-amide 5-Chloro-1H-indole-2-carboxylic acid (9-diethylcarbamoyl-3,4-dihydro-2H-benzo[b][1,4]dioxepin-7-yl)-amide 5-Chloro-1H-indole-2-carboxylic acid [9-(pyrrolidine-1-carbonyl)-3,4-dihydro-2H-benzo[b][1,4]dioxepin-7-yl]-amide 5-Chloro-1H-indole-2-carboxylic acid [9-(piperidine-1-carbonyl)-3,4-ihydro-2H-benzo[b][1,4]dioxepin-7-yl]-amide 5-Chloro-1H-indole-2-carboxylic acid [9-(morpholine-4-carbonyl)-3,4-dihydro-2H-benzo[b][1,4]dioxepin-7-yl]-amide 5-Chloro-1H-indole-2-carboxylic acid [9-(2-hydroxyethylcarbamoyl)-3,4-dihydro-2H-benzo[b][1,4]dioxepin-7-yl]-amide 5-Chloro-1H-indole-2-carboxylic acid [9-(3,4-dihydroxypyrrolidine-1-carbonyl)-3,4-dihydro-2H-benzo[b][1,4]dioxepin-7-yl]-amide 5-Chloro-1H-indole-2-carboxylic acid [9-(4-methylpiperazine-1-carbonyl)-3,4-dihydro-2H-benzo[b][1,4]dioxepin-7-yl]-amide

Example 12

5-Chloro-1H-indole-2-carboxylic acid [(9-hydroxymethyl)]-3,4-dihydro-2H-benzo[b][1,4]dioxepin-7-yl)-amide

LC MS $AP^+$ 373/375, $AP^-$ 371/373

Example 13

5-Chloro-1H-indole-2-carboxylic acid (9-diethylaminomethyl-3,4-dihydro-2H-benzo[b][1,4]dioxepin-7-yl)-amide

LC MS $AP^+$ 428/430, $AP^-$ 426/428

Example 14

5-Chloro-1H-indole-2-carboxylic acid [(9-aminomethyl)]-3,4-dihydro-2H-benzo[b][1,4]dioxepin-7-yl)-amide

Example 15

5-Chloro-1H-indole-2-carboxylic acid [(9-acetylaminomethyl]-3,4-dihydro-2H-benzo[b][1,4]dioxepin-7-yl)-amide

Example 16

5-Chloro-1H-indole-2-carboxylic acid {9-[(3-methyl-ureido)methyl]-3,4-dihydro-2H-benzo[b][1,4]dioxepin-7-yl}-amide

Example 17

5-Chloro-1H-indole-2-carboxylic acid [9-(methylsulfonylamino-methyl)]-3,4-dihydro-2H-benzo[b][1,4]dioxepin-7-yl)-amide

Example 18

{2-[(5-Chloro-1H-indole-2-carbonyl)-amino]-7,8-dihydro-6H-5-oxa-9-aza-benzocyclohepten-9-yl}-acetic acid ethyl ester 5-Chloroindole-2-carboxylic acid (73 mg, 0.37 mmol, 1 eq.), (2-amino-7,8-dihydro-6H-5-oxa-9-aza-benzocyclohepten-9-yl)-acetic acid ethyl ester (93 mg, 0.37 mmol, 1 eq.), and BOP (163 mg, 0.37 mmol, 1 eq.) were dissolved in 5 mL of anhydrous THF in a round bottom flask. Triethylamine was added in a single portion (0.103 mL, 74 mmol, 2 eq.) and reaction mixture stirred at room temperature for 5 hours. The reaction mixture was then concentrated and the residue purified by preparative TLC in 50% AcOEt/hexane affording 79 mg (50% yield) of the product an off-white crystalline solid. LC MS: AP+ 428/430, AP– 426/428.

Example 19

{2-[(5-Chloro-1H-indole-2-carbonyl)-amino]-7,8-dihydro-6H-5-oxa-9-aza-benzocyclohepten-9-yl}-acetic acid {2-[(5-Chloro-1H-indole-2-carbonyl)-amino]-7,8-dihydro-6H-5-oxa-9-aza-benzocyclohepten-9-yl}-acetic acid ethyl ester (10 mg, 0.023 mmol, 1 eq.) was dissolved in a mixture of 1 mL of MeOH and 1 mL of THF and treated with 1 mL 1N NaOH. The reaction was stirred at room temperature for 3 hrs at which time the solvents were removed by evaporation and the residue acidified with 1N HCl. The precipitate was collected on a filter, dried and purified on preparative TLC in 9:1 $CH_2Cl_2$/MeOH to afford 9 mg of the product as a white solid. LC MS: AP+ 400/402,

Example 20

5-Chloro-1H-indole-2-carboxylic acid [9-(2-oxo-2-pyrrolidin-1-yl-ethyl)-6,7,8,9-tetrahydro-5-oxa-9-aza-benzocyclohepten-2-yl]-amide {2-[(5-Chloro-1H-indole-2-carbonyl)-amino]-7,8-dihydro-6H-5-oxa-9-aza-benzocyclohepten-9-yl}-acetic acid (80 mg) and pyrrolidine (14.2 mg) were dissolved in anhydrous THF. To that solution was added BOP and the resulting mixture treated with triethylamine (40.5 mg). The reaction was stirred overnight at room temperature. The reaction was evaporated and the crude product purified by TLC using EtOAc as solvent to yield 68 mg of the product. LCMS: AP+ 453/455.

Example 21

5-Chloro-1H-indole-2-carboxylic acid [9-(2-hydroxy-ethyl)-6,7,8,9-tetrahydro-5-oxa-9-aza-benzocyclohepten-2-yl]-amide {2-[(5-Chloro-1H-indole-2-carbonyl)-amino]-7,8-dihydro-6H-5-oxa-9-aza-benzocyclohepten-9-yl}-acetic acid (80 mg) was dissolved in THF (3 mL) and treated with 1.0 M $BH_3$/THF at room temperature. The reaction was concentrated in vacuo, diluted with EtOAc and washed with 1N HCl. The crude product was purified by preparative TLC (EtOAc) to yield 27 mg of the product as a crystalline solid. LCMS: AP+ 386/388.

Example 22

5-Chloro-1H-indole-2-carboxylic acid benzo[1,3]dioxol-5-ylamide;
LC MS AP+: 315.

Example 23

5-Chloro-1H-indole-2-carboxylic acid (3,4-dihydro-2H-benzo[b][1,4]dioxepin-7-yl)-amide
LC MS AP+: 343

Example 24

1H-indole-2-carboxylic acid (3,4-dihydro-2H-benzo[b][1,4]dioxepin-7-yl)-amide
LC MS AP+: 309

Example 25

H-indole-2-carboxylic acid Benzo[1,3]dioxol-5-ylamide
LC MS AP+: 281

5-Fluoro-1H-indole-2-carboxylic acid (3,4-dihydro-2H-benzo[b][1,4]dioxepin-7-yl)-amide
LC MS AP+: 327

Example 26

5-Methoxy-1H-indole-2-carboxylic acid (3,4-dihydro-2H-benzo[b][1,4]dioxepin-7-yl)-amide
LC MS AP+: 339

Example 27

5-Bromo-1H-indole-2-carboxylic acid (3,4-dihydro-2H-benzo[b][1,4]dioxepin-7-yl)-amide
LC MS AP+: 387/389

Example 28

5-Methyl-1H-indole-2-carboxylic acid (3,4-dihydro-2H-benzo[b][1,4]dioxepin-7-yl)-amide
LC MS AP+: 323

Example 29

6-Methoxy-1H-indole-2-carboxylic acid (3,4-dihydro-2H-benzo[b][1,4]dioxepin-7-yl)-amide
LC MS AP+: 339

Example 30

8-[(5-Chloro-1H-indole-2-carbonyl)-amino]-3,4-dihydro-2H-benzo[b][1,4]dioxepine-6-carboxylic acid methyl ester
LC MS AP$^+$: 401

Example 31

8-[(5-Chloro-1H-indole-2-carbonyl)-amino]-3,4-dihydro-2H-benzo[b][1,4]dioxepine-6-carboxylic acid
LC MS AP$^+$: 387

Example 32

2-Chloro-6H-thieno[2,3-b]pyrrole-5-carboxylic acid (3,4-dihydro-2H-benzo[b][1,4]dioxepin-7-yl)-amide
LC MS AP$^+$: 349

Example 33

5-Chloro-1H-indole-2-carboxylic acid (9-nitro-3,4-dihydro-2H-benzo[b][1,4]dioxepin-7-yl)-amide
LC MS AP$^+$: 343

Example 34

5-Chloro-1H-indole-2-carboxylic acid (9-hydroxymethyl-3,4-dihydro-2H-benzo[b][1,4]dioxepin-7-yl)-amide
LC MS AP$^+$: 373

Example 35

5-Chloro-1H-indole-2-carboxylic acid (9-amino-3,4-dihydro-2H-benzo[b][1,4]dioxepin-7-yl)-amide
LC MS AP$^+$: 358

Example 36

5-Chloro-1H-indole-2-carboxylic acid (9-dimethylcarbamoyl-3,4-dihydro-2H-benzo[b][1,4]dioxepin-7-yl)-amide
LC MS AP$^+$: 414

Example 37

5-Chloro-1H-indole-2-carboxylic acid (9-diethylcarbamoyl-3,4-dihydro-2H-benzo[b][1,4]dioxepin-7-yl)-amide
LC MS AP$^+$: 442

Example 38

5-Chloro-1H-indole-2-carboxylic acid [9-(pyrrolidine-1-carbonyl)-3,4-dihydro-2H-benzo[b][1,4]dioxepin-7-yl]-amide
LC MS AP$^+$: 440

Example 39

5-Chloro-1H-indole-2-carboxylic acid [9-(piperidine-1-carbonyl)-3,4-dihydro-2H-benzo[b][1,4]dioxepin-7-yl]-amide
LC MS AP$^+$: 454

Example 40

5-Chloro-1H-indole-2-carboxylic acid [9-(morpholine-4-carbonyl)-3,4-dihydro-2H-benzo[b][1,4]dioxepin-7-yl]-amide
LC MS AP$^+$: 456

Example 41

5-Chloro-1H-indole-2-carboxylic acid [9-(2-hydroxy-ethylcarbamoyl)-3,4-dihydro-2H-benzo[b][1,4]dioxepin-7-yl]-amide
LC MS AP$^+$: 430

Example 42

5-Chloro-1H-indole-2-carboxylic acid [9-(3,4-dihydroxy-pyrrolidine-1-carbonyl)-3,4-dihydro-2H-benzo[b][1,4]dioxepin-7-yl]-amide
LC MS AP$^+$: 472

Example 43

5-Chloro-1H-indole-2-carboxylic acid (9-methoxymethyl-3,4-dihydro-2H-benzo[b][1,4]dioxepin-7-yl)-amide
LC MS AP$^+$: 387

Example 44

5-Chloro-1H-indole-2-carboxylic acid (9-carbamoyl-3,4-dihydro-2H-benzo[b][1,4]dioxepin-7-yl)-amide
LC MS AP$^+$: 386

Example 45

5-Chloro-1H-indole-2-carboxylic acid [9-(4-methyl-piperazine-1-carbonyl)-3,4-dihydro-2H-benzo[b][1,4]dioxepin-7-yl]-amide
LC MS AP$^+$: 469

Example 46

5-Chloro-1H-indole-2-carboxylic acid (9-acetylamino-3,4-dihydro-2H-benzo[b][1,4]dioxepin-7-yl)-amide
LC MS AP$^+$: 400

Example 47

5-Chloro-1H-indole-2-carboxylic acid (9-dimethylamino-3,4-dihydro-2H-benzo[b][1,4]dioxepin-7-yl)-amide
LC MS AP$^+$: 386

Example 48

{8-[(5-Chloro-1H-indole-2-carbonyl)-amino]-3,4-dihydro-2H-benzo[b][1,4]dioxepin-6-ylamino}-acetic acid ethyl ester
LC MS AP$^+$: 444

Example 49

5-Chloro-1H-indole-2-carboxylic acid [9-(2,2,2-trifluoro-acetylamino)-3,4-dihydro-2H-benzo[b][1,4]dioxepin-7-yl]-amide
LC MS AP$^+$: 454

Example 50

5-Chloro-1H-indole-2-carboxylic acid (9-methanesulfonylamino-3,4-dihydro-2H-benzo[b][1,4]dioxepin-7-yl)-amide
LC MS AP$^+$: 436

Example 51

5-Chloro-1H-indole-2-carboxylic acid [9-(2-Chloro-acetylamino)-3,4-dihydro-2H-benzo[b][1,4]dioxepin-7-yl]-amide
LC MS AP⁺: 435

Example 52

5-Chloro-1H-indole-2-carboxylic acid (9-diethylaminomethyl-3,4-dihydro-2H-benzo[b][1,4]dioxepin-7-yl)-amide
LC MS AP⁺: 428

Example 53

5-Chloro-1H-indole-2-carboxylic acid (9-dimethylaminomethyl-3,4-dihydro-2H-benzo[b][1,4]dioxepin-7-yl)-amide
LC MS AP⁺: 400

Example 54

5-Chloro-1H-indole-2-carboxylic acid {9-[(2-hydroxy-ethylamino)-methyl]-3,4-dihydro-2H-benzo[b][1,4]dioxepin-7-yl}-amide
LC MS AP⁺: 416

Example 55

5-Chloro-1H-indole-2-carboxylic acid (9-piperidin-1-ylmethyl-3,4-dihydro-2H-benzo[b][1,4]dioxepin-7-yl)-amide
LC MS AP⁺: 440

Example 56

5-Chloro-1H-indole-2-carboxylic acid (9-morpholin-4-ylmethyl-3,4-dihydro-2H-benzo[b][1,4]dioxepin-7-yl)-amide
LC MS AP⁺: 442

Example 57

5-Chloro-1H-indole-2-carboxylic acid [9-(benzylamino-methyl)-3,4-dihydro-2H-benzo[b][1,4]dioxepin-7-yl]-amide
LC MS AP⁺: 462

Example 58

5-Chloro-1H-indole-2-carboxylic acid [9-(3,4-dihydroxy-pyrrolidin-1-ylmethyl)-3,4-dihydro-2H-benzo[b][1,4]dioxepin-7-yl]-amide
LC MS AP⁺: 458

Example 59

5-Chloro-1H-indole-2-carboxylic acid {9-[(2-methoxy-ethylamino)-methyl]-3,4-dihydro-2H-benzo[b][1,4]dioxepin-7-yl}-amide
LC MS AP⁺: 430

Example 60

1H-Indole-2-carboxylic acid (9-hydroxymethyl-3,4-dihydro-2H-benzo[b][1,4]dioxepin-7-yl)-amide
LC MS AP⁺: 339

Example 61

5-Fluoro-1H-indole-2-carboxylic acid (9-hydroxymethyl-3,4-dihydro-2H-benzo[b][1,4]dioxepin-7-yl)-amide
LC MS AP⁺: 357

Example 62

5-Methyl-1H-indole-2-carboxylic acid (9-hydroxymethyl-3,4-dihydro-2H-benzo[b][1,4]dioxepin-7-yl)-amide
LC MS AP⁺: 353

Example 63

5-Chloro-1H-indole-2-carboxylic acid {9-[(2-hydroxy-ethylcarbamoyl)-methyl]-6,7,8,9-tetrahydro-5-oxa-9-aza-benzocyclohepten-2-yl}-amide
LC MS AP⁺: 444

Example 64

5-Chloro-1H-indole-2-carboxylic acid [9-(2-oxo-2-piperidin-1-yl-ethyl)-6,7,8,9-tetrahydro-5-oxa-9-aza-benzocyclohepten-2-yl]-amide
LCMS AP⁺: 468

Example 65

5-Chloro-1H-indole-2-carboxylic acid [9-(2-morpholin-4-yl-2-oxo-ethyl)-6,7,8,9-tetrahydro-5-oxa-9-aza-benzocyclohepten-2-yl]-amide
LCMS: AP⁺: 470

Example 66

5-Chloro-1H-indole-2-carboxylic acid {9-[2-(3,4-dihydroxy-pyrrolidin-1-yl)-2-oxo-ethyl]-6,7,8,9-tetrahydro-5-oxa-9-aza-benzocyclohepten-2-yl}-amide
LCMS: AP⁺: 486

Example 67

5-Chloro-1H-indole-2-carboxylic acid {9-[2-(4-methyl-piperazin-1-yl)-2-oxo-ethyl]-6,7,8,9-tetrahydro-5-oxa-9-aza-benzocyclohepten-2-yl}-amide
LCMS: AP⁺: 483

Example 68

3-(4-Chloro-phenyl)-N-(3,4-dihydro-2H-benzo[b][1,4]dioxepin-7-yl)-acrylamide
LC MS AP⁺: 330

Example 69

3-(4-Chloro-phenyl)-N-(9-hydroxymethyl-3,4-dihydro-2H-benzo[b][1,4]dioxepin-7-yl)-acrylamide
LC MS AP⁺: 360

Example 70

2-Chloro-6H-thieno[2,3-b]pyrrole-5-carboxylic acid (3,4-dihydro-2H-benzo[b][1,4]dioxepin-7-yl)-amide
LC MS AP⁺: 349

Example 71

2-Chloro-6H-thieno[2,3-b]pyrrole-5-carboxylic acid (2,3-dihydro-benzo[1,4]dioxin-6-yl)-amide
LC MS AP⁺: 335

Example 72

2-Chloro-6H-thieno[2,3-b]pyrrole-5-carboxylic acid (9-hydroxymethyl-3,4-dihydro-2H-benzo[b][1,4]dioxepin-7-yl)-amide
LC MS AP⁺: 378/380

Example 73

2-Chloro-6H-thieno[2,3-b]pyrrole-5-carboxylic acid (6,7,8,9-tetrahydro-5-oxa-9-aza-benzocyclohepten-2-yl)-amide
LC MS AP+: 348

Example 74

2-Chloro-6H-thieno[2,3-b]pyrrole-5-carboxylic acid [1,5-bis-(toluene-4-sulfonyl)-2,3,4,5-tetrahydro-1H-benzo[b][1,4]diazepin-7-yl]-amide
LC MS AP+: 475

Example 75

2-Chloro-6H-thieno[2,3-b]pyrrole-5-carboxylic acid (9-methyl-6,7,8,9-tetrahydro-5-oxa-9-aza-benzocyclohepten-2-yl)-amide
LC MS AP+:362

Example 76

2-Chloro-6H-thieno[2,3-b]pyrrole-5-carboxylic acid [9-(4-methyl-piperazine-1-carbonyl)-3,4-dihydro-2H-benzo[b][1,4]dioxepin-7-yl]-amide
LC MS AP+: 475

Example 77

5-Chloro-1H-indole-2-carboxylic acid (3,4-dihydro-2H-benzo[b][1,4]dioxepin-7-yl)-amide

Example 78

5-Fluoro-1H-indole-2-carboxylic acid (3,4-dihydro-2H-benzo[b][1,4]dioxepin-7-yl)-amide

Example 79

5-Methyl-1H-indole-2-carboxylic acid (3,4-dihydro-2H-benzo[b][1,4]dioxepin-7-yl)-amide

Example 80

8-[(5-Chloro-1H-indole-2-carbonyl)-amino]-3,4-dihydro-2H-benzo[b][1,4]dioxepine-6-carboxylic acid

Example 81

5-Chloro-1H-indole-2-carboxylic acid (9-hydroxymethyl-3,4-dihydro-2H-benzo[b][1,4]dioxepin-7-yl)-amide

Example 82

5-Chloro-1H-indole-2-carboxylic acid (9-amino-3,4-dihydro-2H-benzo[b][1,4]dioxepin-7-yl)-amide

Example 83

5-Chloro-1H-indole-2-carboxylic acid (9-diethylcarbamoyl-3,4-dihydro-2H-benzo[b][1,4]dioxepin-7-yl)-amide

Example 84

5-Chloro-1H-indole-2-carboxylic acid [9-(2-hydroxy-ethylcarbamoyl)-3,4-dihydro-2H-benzo[b][1,4]dioxepin-7-yl]-amide
LC MS AP+: 430

Example 85

5-Chloro-1H-indole-2-carboxylic acid [9-(3,4-dihydroxy-pyrrolidine-1-carbonyl)-3,4-dihydro-2H-benzo[b][1,4]dioxepin-7-yl]-amide
LC MS AP+: 472

Example 86

5-Chloro-1H-indole-2-carboxylic acid (9-methoxymethyl-3,4-dihydro-2H-benzo[b][1,4]dioxepin-7-yl)-amide
LC MS AP+: 387

Example 87

5-Chloro-1H-indole-2-carboxylic acid [9-(4-methyl-piperazine-1-carbonyl)-3,4-dihydro-2H-benzo[b][1,4]dioxepin-7-yl]-amide
LC MS AP+: 469

Example 88

5-Chloro-1H-indole-2-carboxylic acid (9-methanesulfonylamino-3,4-dihydro-2H-benzo[b][1,4]dioxepin-7-yl)-amide
LC MS AP+: 436

Example 89

5-Chloro-1H-indole-2-carboxylic acid {9-[(2-hydroxy-ethylamino)-methyl]-3,4-dihydro-2H-benzo[b][1,4]dioxepin-7-yl}-amide
LC MS AP+: 416

Example 90

5-Chloro-1H-indole-2-carboxylic acid [9-(3,4-dihydroxy-pyrrolidin-1-ylmethyl)-3,4-dihydro-2H-benzo[b][1,4]dioxepin-7-yl]-amide
LC MS AP+: 458

Example 91

5-Fluoro-1H-indole-2-carboxylic acid (9-hydroxymethyl-3,4-dihydro-2H-benzo[b][1,4]dioxepin-7-yl)-amide
LC MS AP+: 357

Example 92

5-Methyl-1H-indole-2-carboxylic acid (9-hydroxymethyl-3,4-dihydro-2H-benzo[b][1,4]dioxepin-7-yl)-amide
LC MS AP+: 353

Example 93

5-Chloro-1H-indole-2-carboxylic acid {9-[(2-hydroxy-ethylcarbamoyl)-methyl]-6,7,8,9-tetrahydro-5-oxa-9-aza-benzocyclohepten-2-yl}-amide
LC MS AP+: 444

Example 94

5-Chloro-1H-indole-2-carboxylic acid [9-(2-oxo-2-piperidin-1-yl-ethyl)-6,7,8,9-tetrahydro-5-oxa-9-aza-benzocyclohepten-2-yl]-amide
LCMS AP+: 468

Example 95

5-Chloro-1H-indole-2-carboxylic acid [9-(2-morpholin-4-yl-2-oxo-ethyl)-6,7,8,9-tetrahydro-5-oxa-9-aza-benzocyclohepten-2-yl]-amide
LCMS: AP$^+$: 470

Example 96

5-Chloro-1H-indole-2-carboxylic acid {9-[2-(3,4-dihydroxy-pyrrolidin-1-yl)-2-oxo-ethyl]-6,7,8,9-tetrahydro-5-oxa-9-aza-benzocyclohepten-2-yl}-amide
LCMS: AP$^+$: 486

Example 97

5-Chloro-1H-indole-2-carboxylic acid {9-[2-(4-methyl-piperazin-1-yl)-2-oxo-ethyl]-6,7,8,9-tetrahydro-5-oxa-9-aza-benzocyclohepten-2-yl}-amide
LCMS: AP$^+$: 483

Example 98

3-(4-Chloro-phenyl)-N-(3,4-dihydro-2H-benzo[b][1,4]dioxepin-7-yl)-acrylamide
LC MS AP$^+$: 330

Example 99

2-Chloro-6H-thieno[2,3-b]pyrrole-5-carboxylic acid (3,4-dihydro-2H-benzo[b][1,4]dioxepin-7-yl)-amide
LC MS AP$^+$: 348

Example 100

2-Chloro-6H-thieno[2,3-b]pyrrole-5-carboxylic acid (2,3-dihydro-benzo[1,4]dioxin-6-yl)-amide
LC MS AP$^+$: 335

Example 101

2-Chloro-6H-thieno[2,3-b]pyrrole-5-carboxylic acid (9-hydroxymethyl-3,4-dihydro-2H-benzo[b][1,4]dioxepin-7-yl)-amide
LC MS AP$^+$: 378/380

Example 102

2-Chloro-6H-thieno[2,3-b]pyrrole-5-carboxylic acid (6,7,8,9-tetrahydro-5-oxa-9-aza-benzocyclohepten-2-yl)-amide
LC MS AP$^+$: 348

Example 103

2-Chloro-6H-thieno[2,3-b]pyrrole-5-carboxylic acid [1,5-bis-(toluene-4-sulfonyl)-2,3,4,5-tetrahydro-1H-benzo[b][1,4]diazepin-7-yl]-amide
LC MS AP$^+$: 656

Example 104

2-Chloro-6H-thieno[2,3-b]pyrrole-5-carboxylic acid (9-methyl-6,7,8,9-tetrahydro-5-oxa-9-aza-benzocyclohepten-2-yl)-amide
LC MS AP$^+$: 362

Example 105

2-Chloro-6H-thieno[2,3-b]pyrrole-5-carboxylic acid [9-(4-methyl-piperazine-1-carbonyl)-3,4-dihydro-2H-benzo[b][1,4]dioxepin-7-yl]-amide
LC MS AP$^+$: 475

Example 106

Methyl-3-aminosalicylate

Methyl-3-nitrosalicylat (4.93 grams, 25 mmol) dissolved in 50 mL of methanol was placed in a Parr bottle together with 200 mg of 10% Pd/C and hydrogenated at room temperature at 45 psi for 2 hours. The reaction was then filtered through celite, concentrated to dryness and the product dried in vacuo. Yield 4.17 gram (99% light green needles, M+168, single spot on TLC.

Example 107

3-Formylamino-2-hydroxy-benzoic acid methyl ester

To a solution of methyl-3-aminosalicylate (3.34 grams, 20 mmol) in concentrated formic acid (20 mL) was added solid sodium formate (1.36 grams, 20 mmol, 1 eq.) and the resulting suspension stirred under reflux for 2 hours. The precipitate was filtered at room temperature and washed with water until neutral. After drying on air, 3.595 grams (92%) light brown crystals were collected. M+196, M−194.

Example 108

9-Formyl-6,7,8,9-tetrahydro-5-oxa-9-aza-benzocycloheptene-4-carboxylic acid methyl ester Potassium carbonate was ground and flame dried prior to each use. 3-formylamino-2-hydroxy-benzoic acid methyl ester compound (1.952 grams, 10 mmol) and potassium carbonate (2.764 grams, 20 mmol, 2 eq.) were placed in a flask together with 100 mL of anhydrous DMF. Heated to 120° C. for 1 hour. 1-bromo-3-chloropropane (1 mL, 10 mmol, 1 eq.) was added to the reaction mixture in several portions at 120° C. and the reaction heated for an additional 3 hours. The reaction was monitored on TLC (ethyl acetate). After cooling, the reaction mixture was stripped to a minimal volume, diluted with water and extracted three times with ethyl acetate. The combined organic portions were washed with water, brine and dried over magnesium sulfate. Filtration and solvent removal afforded crude product as a thick brown syrup (1.78 grams) which was chromatographed on silica gel using 30% ethyl acetate in hexane as eluent. The product was obtained in 67% yield as light yellow solid. M+236.

Example 109

9-Formyl-2-nitro-6,7,8,9-tetrahydro-5-oxa-9-aza-benzocycloheptene-4-carboxylic acid methyl ester The compound 9-formyl-6,7,8,9-tetrahydro-5-oxa-9-aza-benzocycloheptene-4-carboxylic acid methyl ester (705 mg, 3 mmol) was dissolved in concentrated sulfuric acid (30 mL) and the resulting deep blue solution cooled to 0° C. in an ice bath. It was then treated with 90% fuming nitric acid dropwise (1.5 mL), allowed to warm up to room temperature and stirred for additional 2 hours. The reaction mixture was then carefully poured over 500 mL of ice and the pink precipitate was filtered at room temperature, washed thoroughly with water and dried in vacuo. The crude product was recrystallized from boiling acetonitrile. Yield 702 mg (83%) light yellow crystals, M−280.

Example 110

2-Nitro-6,7,8,9-tetrahydro-5-oxa-9-aza-benzocycloheptene-4-carboxylic acid methyl ester The previously prepared nitroamide 9-formyl-2-nitro-6,7,8,9-tetrahydro-5-oxa-9-aza-benzocycloheptene-4- carboxylic acid methyl ester (4.76 grams, 17 mmol) was suspended in 1N HCl and heated to 100° C. for 2 hours. After cooling to room temperature, the pH of the reaction mixture was adjusted to 12 with 1N NaOH. The precipitate formed was extracted with ethyl acetate. The latter was dried over anhydrous magnesium sulfate, filtered and evaporated.

Example 111

2-Amino-6,7,8,9-tetrahydro-5-oxa-9-aza-benzocycloheptene-4-carboxylic acid methyl ester To a 1.51 gram (6 mmol) of the nitro methyl ester compound 2-nitro-6,7,8,9-tetrahydro-5-oxa-9-aza-benzocycloheptene-4-carboxylic acid methyl ester in a 100 mL of 1:1 mixture of methanol:THF, a 50 mg of 10% Pd/C and solid ammonium formate (1.89 gram, 30 mmol, 5 eq.) was added carefully under nitrogen. The reaction mixture was stirred at room temperature in a capped vial for 2 hours, dilute with 300 mL diethylether and through celite. The solvent removal afforded 1.71 grams of crude product, which was flash chromatographed on silica gel in ethyl acetate. Yield 1.29 grams clear syrup (96%), M+223.

Example 112

2-[(5-Chloro-1H-indole-2-carbonyl)-amino]-6,7,8,9-tetrahydro-5-oxa-9-aza-benzocycloheptane-4-carboxylic acid methyl ester

M+ 400/402, M−398/400.

Example 113

2-[(5-Chloro-1H-indole-2-carbonly)-amino]-6,7,8,9-tetrahydro-5-oxa-9-aza-benzocycloheptene-4-carboxylic acid

M−385/387.

Example 114

5-Chloro-1H-indole-2-carboxylic acid (4-hydroxymethyl-6,7,8,9-tetrahydro-5-oxa-9-aza-benzocycloheptene-2-yl)-amide

M+372/374, M−370/372.

Example 115

N,N'-ditosyl-4-nitro-o-phenylenediamine 4-nitro-o-phenylenediamine (15.4 grams, 100 mmol) was dissolved in anhydrous pyridine (70 mL) at 45° C. p-Toluenesulfonyl chloride was added to the reaction mixture in 5 gram portions over the period of 30 minutes. The reaction was then heated to 100° C. for 4 hours. After cooling to room temperature, the mixture was poured into ice/water and this was extracted 3 times with methylene chloride. The combined organic portions were washed with water and brine and dried over anydrous sodium sulfate. Filtration and concentration afforded crude product, which was triturated with hot ethanol to give 32.5 grams of product as yellow powder (70%). M+462.

Example 116

7-Nitro1,5-bis-(toluene-4-sulfonyl)-2,3,4,5-tetrahydro-1H-benzo[b][1,4]diazepine The 3-neck round bottom flask equipped with reflux condenser, nitrogen inlet and mechanical stirrer was flame dried and cooled in a stream of dry nitrogen. The flask was then charged with 32 mL of anhydrous n-butanol and sodium metal flakes (0.46 grams, 20 mmol, 2 eq.). This was stirred at room temperature until all the metal dissolved and evolution of hydrogen gas ceased. The solid ditosylate N,N'-ditosyl-4-nitro-o-phenylenediamine was then added in portions and the solution heated to 125° C. until an orange thick paste formed. The 1,3-dibromopropane (1.52 mL, 15 mmol, 1.5 eq.) was added dropwise as a solution in 5 mL of anhydrous n-butanol and the solution heated to 125° C. overnight. The reaction was monitored by TLC. Another equivalent of 1,3-dibromopropane was added and the solution heated for an additional 12 hours. The reaction was cooled to room temperature, concentrated in vacuo and the residue combined wit 100 mL of 3% NaOH and refluxed for one hour. The hot solution was filtered, the filter cake washed thoroughly with warm 1% NaOH and water until neutral. The crude product was dried in vacuo and recrystallized form boiling acetic acid. Yield 1.238 grams (23%) of yellow powder. M+502, M−345 (loss of Ts).

Example 117

7-Amino-1,5-bis-(toluene-4-sulfonyl)-2,3,4,5-tetrahydro-1H-benzo[b][1,4]diazepine The ditosylate 7-Nitro5-bis-(toluene-4-sulfonyl)-2,3,4,5-tetrahydro-1H-benzo[b][1,4]diazepine (502 mg, 1 mmol), 10% Pd/C (20 mg) and ammonium formate (315 mg, 5 mmol, 5 eq.) was dissolved in a mixture of 5 mL of methanol and 5 mL THF and stirred in a capped flask at room temperature for 3 hours. The reaction mixture was then diluted with 60 mL of diethylether, filtered through celite and the filtrate concentrated. The crude product was dried in vacuo to give 412 mg (87%) of white powder, M+489. This was used without further purification.

Example 118

5-Chloro-1H-indole-2-carboxylic acid [1,5-bis-(toluene-4-sulfonyl)-2,3,4-tetrahydro-1H-benzo[b][1,4]diazepine-7-yl]amide

M+652/650, M−648,650.

Example 119

2-Chloro-6H-thieno[2,3-b]pyrrole-5-carboxylic acid [1,5-bis-(toluene-4-sulfonyl)-2,3,4,5-tetrahydro-1H-benzo[b][1,4]diazepin-7-yl]-amide M+655/657, M−499 (loss of Ts group).

What is claimed is:

1. A compound of the formula

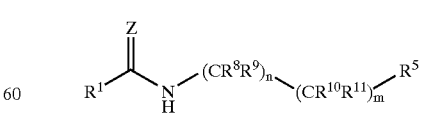

I or the pharmaceutically acceptable salt thereof; wherein n is 0, 1, 2, 3 or 4;

m is 0, 1, 2, 3 or 4;

Z is oxygen or sulfur;

R¹ is (i) [indole structure with (R²)ₐ substitution, attached at 2-position]

(ii) [thieno-pyrrole structure with R³, R⁴ substituents]

(iii) [styryl/cinnamyl structure with (R²)ₐ phenyl]

wherein the dashed lines represent optional double bonds;
a is 1, 2 or 3;
each $R^2$ is independently hydrogen, halo, hydroxy, amino, nitro, $(C_1-C_6)$alkoxy, cyano, C(O)H or $(C_1-C_6)$alkyl optionally substituted by one to three fluoro atoms;
$R^3$ is hydrogen, halo, cyano, $(C_1-C_6)$alkyl or $(C_1-C_3)$alkynyl;
$R^4$ is hydrogen, halo, cyano or $(C_1-C_6)$alkyl;
$R^5$ is (iv) [bicyclic structure with A, B, E, X, Y and R¹², R¹³, R¹⁴ substituents]

wherein the dashed lines represent optional double bonds;
A, B and E are $CR^{15}$;
X and Y are oxygen;
$R^8$, $R^9$, $R^{10}$ and $R^{11}$ are each independently hydrogen or $(C_1-C_6)$alkyl;
$R^{12}$ is hydrogen, $HC(O)(C_0-C_6)$alkyl, carboxy$(C_0-C_3)$alkyl, $R^{17}R^{18}N$—C(O)—$(C_0-C_3)$alkyl, hydroxy$(C_1-C_3)$alkyl, $R^{17}(C_1-C_3)$alkyl, $R^{17}R^{18}N(C_0-C_3)$alkyl, $(C_1-C_6)$alkyl-C(O)—NH, $(C_6-C_{10})$aryl-C(O)—NH, $(C_6-C_{10})$aryl$(C_1-C_6)$alkyl-C(O)—NH, $(C_2-C_9)$heteroaryl$(C_1-C_6)$alkyl-C(O)—NH, $(C_1-C_6)$alkylaminocarbonylamino, $(C_6-C_{10})$arylaminocarbonylamino, $(C_6-C_{10})$aryl$(C_1-C_6)$alkylaminocarbonylamino, $(C_2-C_9)$heteroaryl$(C_1-C_6)$alkylaminocarbonylamino, $(C_1-C_6)$alkylsulfonylamino, $(C_6-C_{10})$aryl$(C_1-C_6)$alkylsulfonylamino, $(C_2-C_9)$heteroarylsulfonylamino, $(C_2-C_9)$heteroaryl$(C_1-C_6)$alkylsulfonylamino, $(C_1-C_6)$alkylsulfonyl N$((C_1-C_6)$alkyl), $(C_6-C_{10})$aryl$(C_1-C_6)$alkylsulfonyl N$((C_1-C_6)$alkyl), $(C_2-C_9)$heteroarylsulfonyl N$((C_1-C_6)$alkyl), $(C_2-C_9)$heteroaryl$(C_1-C_6)$alkylsulfonyl N$((C_1-C_6)$alkyl), $(C_3-C_7)$cycloalkylamino, $((C_3-C_7)$cycloalkyl)$_2$amino, $(C_3-C_7)$cycloalkylcarbonylamino, $(C_6-C_{10})$aryl$(C_3-C_7)$cycloalkylcarbonylamino, $(C_2-C_9)$heteroaryl$(C_3-C_7)$cycloalkylcarbonylamino, $(C_3-C_7)$cycloalkylaminocarbonylamino, $(C_6-C_{10})$aryl$(C_3-C_7)$cycloalkylaminocarbonylamino, $(C_2-C_9)$heteroaryl$(C_3-C_7)$cycloalkylaminocarbonylamino, $(C_3-C_7)$cycloalkylsulfonylamino, $(C_6-C_{10})$aryl$(C_3-C_7)$cycloalkylsulfonylamino, $(C_2-C_9)$heteroaryl$(C_3-C_7)$cycloalkylsulfonylamino, $(C_3-C_7)$cycloalkylsulfonyl N$((C_3-C_7)$cycloalkyl), $(C_6-C_{10})$aryl$(C_3-C_7)$cycloalkylsulfonyl N$((C_3-C_7)$cycloalkyl, $(C_2-C_9)$heteroarylsulfonyl N$((C_3-C_7)$cycloalkyl), $(C_2-C_9)$heteroaryl$(C_3-C_7)$cycloalkylsulfonyl N$((C_3-C_7)$cycloalkyl), $(C_1-C_6)$alkyl $S(O)_c$, $(C_3-C_7)$cycloalkyl $S(O)_c$, $(C_6-C_{10})$aryl$(C_1-C_6)$alkyl $S(O)_c$, $(C_6-C_{10})$aryl $S(O)_c$, $(C_1-C_6)$alkylamino $S(O)_c$, $(C_1-C_6)$arylamino $S(O)_c$, $(C_6-C_{10})$aryl$C_1-C_6$alkylamino $S(O)_c$ wherein c is 0, 1 or 2;
$R^{13}$ is hydrogen or $(C_1-C_6)$alkyl;
$R^{14}$ is hydrogen, hydroxy, $(C_1-C_6)$alkoxy, $(C_6-C_{10})$aryloxy or $NR^{17}R^{18}$;
$R^{15}$ is hydrogen, $(C_1-C_6)$alkylcarbonylcarboxy, hydroxy$(C_1-C_6)$alkyl, $(C_1-C_6)$alkyl piperazinylcarbonyl or piperidinylcarbonyl;
$R^{17}$ and $R^{18}$ are each independently hydrogen, $(C_1-C_6)$alkyl, $(C_6-C_{10})$aryl$(C_1-C_6)$alkyl and $(C_2-C_9)$heteroaryl$(C_1-C_6)$alkyl.

2. A compound of claim 1, wherein R¹ is (i) [indole structure with (R²)ₐ substitution]

wherein a is 1 or 2; and each $R^2$ is independently halo, amino or $(C_1-C_6)$alkyl optionally substituted by one to three fluoro atoms.

3. A compound of claim 1, wherein n is 0, 1, 2 or 3; m is 0, 1, 2 or 3; and Z is oxygen.

4. A compound according to claim 1, wherein $R^{12}$ is hydrogen, $(C_1-C_6)$alkyl, hydroxy$(C_1-C_3)$alkyl or carboxy.

5. A compound of claim 1, wherein R¹ is (i) [indole structure with (R²)ₐ substitution]

wherein a is 1 or 2; and each $R^2$ is independently halo, amino or $(C_1-C_6)$alkyl optionally substituted by one to three fluoro atoms; n is 0, 1, 2 or 3; m is 0, 1, 2 or 3; Z is oxygen and $R^{12}$ is H, $(C_1-C_6)$alkyl, hydroxy$(C_1-C_6)$alkyl or carboxy.

6. A compound of claim 1, wherein said compound is selected from the group consisting of:

5-Chloro-1H-indole-2-carboxylic acid (9-methanesulfonylamino-3,4-dihydro-2H-benzo[b][1,4]dioxepin-7-yl)-amide;

5-Chloro-1H-indole-2-carboxylic acid (9-hydroxymethyl-3,4-dihydro-2H-benzo[b][1,4]dioxepin-7-yl)-amide;

{8-[(5-Chloro-1H-indole-2-carbonyl)-amino]-3,4-dihydro-2H-benzo[b][1,4]dioxepin-6-ylamino}-acetic acid ethyl ester;

5-Chloro-1H-indole-2-carboxylic acid (9-amino-3,4-dihydro-2H-benzo[b][1,4]dioxepin-7-yl)-amide;

5-Methyl-1H-indole-2-carboxylic acid (9-hydroxymethyl-3,4-dihydro-2H-benzo[b][1,4]dioxepin-7-yl)-amide;

5-Chloro-1H-indole-2-carboxylic acid [9-(2-hydroxyethylcarbamoyl)-3,4-dihydro-2H-benzo[b][1,4]dioxepin-7-yl]-amide;

5-Chloro-1H-indole-2-carboxylic acid (3,4-dihydro-2H-benzo[b][1,4]dioxepin-7-yl)-amide;

5-Chloro-1H-indole-2-carboxylic acid (9-dimethylcarbamoyl-3,4-dihydro-2H-benzo[b][1,4]dioxepin-7-yl)-amide;

5-Bromo-1H-indole-2-carboxylic acid (3,4-dihydro-2H-benzo[b][1,4]dioxepin-7-yl)-amide;

8-[(5-Chloro-1H-indole-2-carbonyl)-amino]-3,4-dihydro-2H-benzo[b][1,4]dioxepine-6-carboxylic acid;

5-Methyl-1H-indole-2-carboxylic acid (3,4-dihydro-2H-benzo[b][1,4]dioxepin-7-yl)-amide;

5-Chloro-1H-indole-2-carboxylic acid [9-(3,4-dihydroxy-pyrrolidine-1-carbonyl)-3,4-dihydro-2H-benzo[b][1,4]dioxepin-7-yl]-amide;

1H-Indole-2-carboxylic acid (9-hydroxymethyl-3,4-dihydro-2H-benzo[b][1,4]dioxepin-7-yl)-amide;

1H-Indole-2-carboxylic acid (3,4-dihydro-2H-benzo[b][1,4]dioxepin-7-yl)-amide;

5-Chloro-1H-indole-2-carboxylic acid [9-(4-methyl-piperazine-1-carbonyl)-3,4-dihydro-2H-benzo[b][1,4]dioxepin-7-yl]-amide; and 5-Fluoro-1H-indole-2-carboxylic acid (3,4-dihydro-2H-benzo[b][1,4]dioxepin-7-yl)-amide.

7. A pharmaceutical composition comprising a compound of claim 1 or a pharmaceutically acceptable salt thereof and a pharmaceutically acceptable carrier or diluent.

8. A method of treating atherosclerosis, diabetes, insulin resistance, diabetic neuropathy, diabetic nephropathy, diabetic retinopathy, cataracts, hypercholesterolemia, hypertriglyceridemia, hyperlipidemia, hyperglycemia, hypertension, tissue ischemia or myocardial ischemia in a mammal, the method comprising administering to said mammal suffering from atherosclerosis, diabetes, insulin resistance, diabetic neuropathy, diabetic nephropathy, diabetic retinopathy, cataracts, hypercholesterolemia, hypertriglyceridemia, hyperlipidemia, hyperglycemia, hypertension, tissue ischemia or myocardial ischemia a compound of claim 1, a pharmaceutically acceptable salt thereof or a pharmaceutical composition comprising said compound of claim 1.

9. A method of inhibiting glycogen phosphorylase in a mammal, the method comprising administering to said mammal in need of glycogen phosphorylase inhibition a compound of claim 1, a pharmaceutically acceptable salt thereof or a pharmaceutical composition comprising said compound of claim 1.

10. A method of treating diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis or tissue ischemia, the method comprising the step of administering to a patient suffering from diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis or tissue ischemia a compound of claim 1 or a pharmaceutically acceptable salt thereof in combination with at least one additional compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis or tissue ischemia.

* * * * *